(12) United States Patent
Parvatiyar et al.

(10) Patent No.: US 8,834,424 B2
(45) Date of Patent: Sep. 16, 2014

(54) MEDICAL ARTICLE SECUREMENT DEVICE

(75) Inventors: Anu Parvatiyar, Lilburn, GA (US); Rafael V. Andino, Grayson, GA (US); Howard M. Tanner, Loganville, GA (US); John Gohde, Decatur, GA (US)

(73) Assignee: Venetec International, Inc., Covington, GA (US)

( * ) Notice: Subject to any disclaimer, the term of this patent is extended or adjusted under 35 U.S.C. 154(b) by 306 days.

(21) Appl. No.: 13/215,783

(22) Filed: Aug. 23, 2011

(65) Prior Publication Data
US 2013/0053785 A1 Feb. 28, 2013

(51) Int. Cl.
*A61M 5/32* (2006.01)
*A61M 25/02* (2006.01)

(52) U.S. Cl.
CPC .......... *A61M 25/02* (2013.01); *A61M 2025/024* (2013.01); *A61M 2025/028* (2013.01); *A61M 2025/0273* (2013.01)
USPC ........................................................ 604/174

(58) Field of Classification Search
USPC .................................. 604/174, 177, 178, 180
See application file for complete search history.

(56) References Cited

U.S. PATENT DOCUMENTS

| | | | |
|---|---|---|---|
| 3,782,383 A | | 1/1974 | Thompson et al. |
| 4,129,128 A | * | 12/1978 | McFarlane .................... 604/180 |
| 4,250,880 A | * | 2/1981 | Gordon .......................... 604/180 |
| 5,735,821 A | * | 4/1998 | Dobkin .......................... 604/174 |
| 5,916,200 A | | 6/1999 | Eppley et al. |
| 7,160,270 B2 | * | 1/2007 | West et al. .................... 604/174 |
| 2004/0204685 A1 | | 10/2004 | Wright et al. |
| 2007/0142784 A1 | * | 6/2007 | Dikeman et al. .............. 604/174 |
| 2007/0142785 A1 | * | 6/2007 | Lundgaard et al. ........... 604/179 |
| 2011/0264050 A1 | * | 10/2011 | Henry et al. .................. 604/177 |

FOREIGN PATENT DOCUMENTS

| | | |
|---|---|---|
| WO | WO 00/48658 | 8/2000 |
| WO | WO 2004/016309 | 2/2004 |
| WO | WO 2004/022140 | 3/2004 |
| WO | WO 2011/133818 | 10/2011 |

OTHER PUBLICATIONS

International Search Report and Written Opinion from related International Application No. PCT/US2012/051760, mailed Nov. 2, 2012.

* cited by examiner

*Primary Examiner* — Kami A Bosworth
(74) *Attorney, Agent, or Firm* — Knobbe Martens Olson & Bear, LLP

(57) ABSTRACT

A securement device includes a retainer having at least one retention member extending into a channel of the retainer. The retention member is coupled to the retainer and includes a distal end. The distal end is movable relative to the retainer. The retention member can extend from the body and/or supports of the retainer on opposite sides of the channel axis. In some embodiments, a first set of retention members extends from a first support and a second set of retention members extends from the other support. The first set and the second set of retention members can be staggered laterally along the channel axis such that the lateral sides of the retainer are asymmetric which allow the same retainer to secure medical article having different shapes and sizes. The retainer may further include one or more abutment features or pills configured to contact the medical article.

21 Claims, 21 Drawing Sheets

MEDICAL ARTICLE SECUREMENT DEVICE

BACKGROUND

1. Field

This disclosure relates to a securement device used to attach a medical article to a patient.

2. Description of the Related Art

Healthcare providers routinely require access to the vasculature of a patient for delivery or withdrawal of fluids to or from the patient's blood stream. When such access is required over an extended period of time, it is common to introduce a catheter or similar medical article into the bloodstream of the patient. The catheter provides reusable access in order to deliver medication and/or fluids directly into the bloodstream of the patient.

In intravenous applications, a connector, for example, a luer connector, designed for attachment to a medical line can be coupled to a catheter at one end to form part of a catheterization assembly. Such a connector may also include a connector fitting, for example, a spin nut, to lock the medical line to the catheter. In this way the same catheter may be connected to and released from different medical lines in order to exchange the medical lines without the need to introduce multiple intravenous catheters into the patient's vasculature. In some cases, an extension set including a medical tube with a spin nut at one end is connected to the catheter so that the free end of the extension set can be attached to another medical line at a location further away from the insertion site than the catheter.

In order to keep a catheterization assembly or other medical article properly positioned for the duration of treatment, the catheterization assembly or medical article can be secured to the patient in a variety of ways. Most commonly, this involves taping the catheterization assembly or medical article to the patient.

Securing a catheterization assembly with tape upon the patient traditionally has certain drawbacks. The use of tape at the insertion site can retain dirt or other contaminant particles, potentially leading to infection of the patient. Tape also fails to limit catheter motion and, therefore, contributes to motion related complications like phlebitis, infiltration and catheter migration. Additionally, removal of taped dressings can itself cause undesired motion of the catheterization assembly upon the patient.

Taped dressings also require periodic changes. The frequent, often daily, removal and reapplication of adhesive tape to the skin of the patient can excoriate the skin in the area around the dressing. Such repeated applications of tape over the catheterization assembly or medical article can additionally lead to the build up of adhesive residue on the outer surface of the catheterization assembly or medical article. This residue can result in contaminants adhering to the catheterization assembly, increasing the likelihood of infection of the insertion site. This residue can also make the catheterization assembly or medical article stickier and more difficult to handle for healthcare providers.

SUMMARY OF THE INVENTION

The devices, systems, and methods of the present disclosure have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description of Certain Embodiments" one will understand how the features of this invention provide several advantages over traditional medical article securement devices.

One aspect of the present invention is a retainer for securing a medical article. The retainer includes a body member that has a channel formed therethrough. The channel is configured to retain at least a portion of the medical article and has a longitudinal access opening disposed on an underside of the body member to allow at least ingress of a portion of the medical article into the channel. The retainer further includes first and second supports disposed on the underside of the retainer and located on opposite sides of the channel. The retainer further includes at least one retention member pivotably coupled to the body member or the first and second supports and has a distal end. At least a portion of the distal end is disposed in the channel so as to contact an outer surface of the portion of the medical article when the medical article is secured within the retainer.

Another aspect of the present invention is an apparatus for retaining a portion of a medical article. The apparatus includes a body that has a channel extending therethrough about a longitudinal axis. The channel is shaped to retain at least a portion of the medical article. The apparatus further includes a first support and a second support located on the underside of the body and on opposite sides of the channel and a plurality of retention members extending from the first and second supports and into the channel. The plurality of retention members is spaced along the longitudinal axis. Each of the retention members has a secured end and an unsecured end. The unsecured end is movable relative to the secured end. The apparatus further includes a pair of anchors comprising lower adhesive surfaces configured to be secured to the skin of a patient. The anchors support the retainer.

Another aspect of the present invention is a retainer for securing a medical article. The retainer includes a body member that has a channel formed therethrough. The channel is configured to retain at least a portion of the medical article and has a longitudinal access opening disposed on an underside of the body member to allow at least ingress of a portion of the medical article into the channel. The retainer further includes at least one retention member coupled to the body member and has a distal end. At least a portion of the distal end is disposed in the channel so as to contact an outer surface of the portion of the medical article when the medical article is secured within the retainer. The retainer further includes a first support and a second support. Each support is coupled to the body member so as to rotate between a first position and a second position. The first and second supports deflect the body member when in the second position so as to increase a lateral dimension of the longitudinal access opening.

Another aspect of the present invention is a method for releasably anchoring an elongated medical article. The method includes providing a retainer having a body comprising at least one retention member, a channel which extends through at least a portion of the body, and a longitudinal access opening disposed on an underside of the body to allow at least ingress of a portion of the medical article into the channel. The at least one retention member is pivotably coupled to the body so as to move between at least a first position and a second position. The at least one retention member extends into the channel. The method further includes inserting the portion of the medical article through the access opening and into the channel and deflecting the at least one retention member from the first position to the second position so as to secure the medical article in the channel.

BRIEF DESCRIPTION OF THE DRAWINGS

Features of the invention will now be described with reference to the drawings of several embodiments of the present securement device. The illustrated embodiments of the securement devices are intended to illustrate, but not to limit the invention. The drawings contain the following figures.

DETAILED DESCRIPTION OF CERTAIN EMBODIMENTS

Figure 1:
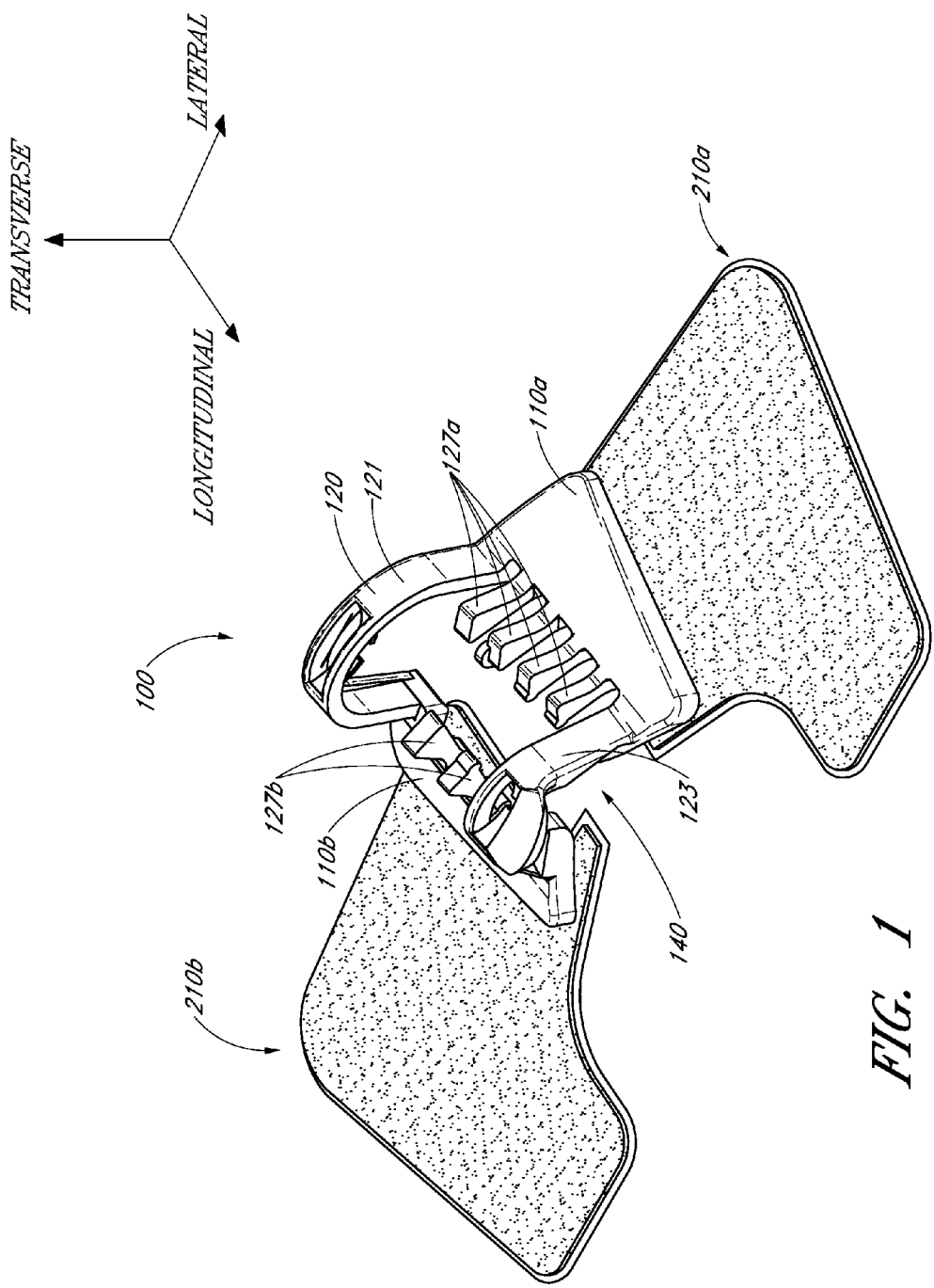
FIG. 1 is a front perspective view of a securement device, including a retainer and anchor pads, in accordance with a preferred embodiment of the present invention.

The following description and examples illustrate certain embodiments of the present securement device disclosed in the context of a catheterization assembly. The catheterization assembly can include a catheter and one or more connectors for attaching the catheter to a medical line. The preferred embodiments of the present invention advantageously provide a securement device for securing a medical article, e.g., one or more components of a catheterization assembly, relative to a patient. The medical articles can cooperate with the retainer of the securement device to arrest movement of the medical article in longitudinal, lateral, and/or transverse directions relative to an insertion site when secured by the securement device. The securement devices accomplish this without meaningfully impairing (i.e., substantially occluding) fluid flow through a lumen of the medical article or impairing insertion of a medical article, for example, a catheter, into a patient.

In some embodiments described below, the retainer can include one or more retention members that extend into the channel of the retainer for engaging the received portion of the catheterization assembly. The retention members can extend from the retainer into the channel. For example, the retention members can have a first end coupled to the retainer and a second free end extending from the retainer into the channel to contact the medical article. In this way, the retention members can be cantilevered relative to the lateral sides of the retainer.

The length of the retention members can vary from retention member to retention member such that they extend into the channel to different degrees or distances. The retention members can be flexible such that they may flex, deflect, or otherwise move relative to each other and the other components of the retainer. In some embodiments, the movement of the unsecured ends of the retention members relative to other retainer components may be facilitated by a living hinge or thinned region near the secured end of the retention member. Thus, a portion of the medical article that is received by the retainer may contact one or more retention members to deflect the contacted retention members away from the axis of the channel while the retained portion of the medical article is positioned within the channel. The deflected retention members may be biased to return to an un-deflected configuration after the portion of the medical article is disposed within the channel.

The retention members can each include an upper facing retention surface for contacting a downward facing contact surface of the retained portion of the medical article. In some embodiments, the retention surface can be contoured or shaped so as to support the medical article within the channel and to inhibit lateral movement of the medical article relative to the retention members. The retention surface can include a plurality of upper facing surfaces separated by one or more contours or edges. The sizes and shapes of the retention surfaces can vary from retention member to retention member from the same retainer.

In some embodiments, the retainer can include a first set of retention members that extend into the channel from a first lateral side and a second set of retention members that extend into the channel from a second lateral side that is opposite to the first side. The first and second sets of retention members can be staggered laterally along the longitudinal axis of the channel such that the first and second lateral sides of the retainer are asymmetric. At least one of the retention members can abut a distal facing contact surface of the catheterization assembly such that distal longitudinal movement of the catheterization assembly is inhibited. For example, one of the retention members can abut a distal side of a radially extending member, e.g., a spin nut, so as to inhibit longitudinal movement of the radially extending member away from the retainer. Thus, the staggered asymmetric configuration of retention members can allow a single retainer to accommodate medical articles having different longitudinal lengths.

In some embodiments described below, the retainer can include one or more base portions extending laterally from a body portion. The one or more base portions can be manipulated relative to the body portion so as to expand a longitudinal access opening to the channel. In this way, the retainer can be manipulated between at least two configurations so as to receive and secure a portion of the medical article.

Although, the embodiments of the securement devices are illustrated with intravenous catheters, connectors, and medical lines, it will be understood by those of skill in the art in view of the present disclosure that the securement devices described herein can be used with other types of medical articles, including, but not limited to catheters and catheter hubs of various designs, either with or without connectors or extension sets, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes, any other sort of fluid supply or medical lines, connector fittings, and scopes, as well as electrical wires or cables connected to external or implanted electronic devices or sensors. The medical articles can each be a single component, e.g., a catheter hub or a connector, or a combination of components, e.g., a catheterization assembly.

One skilled in the art may also find additional applications for the devices, systems, and methods disclosed herein. Accordingly, the illustration and description of the securement devices in connection with a catheter and a connector is merely exemplary of one possible application of the securement devices and techniques disclosed.

Figure 16:
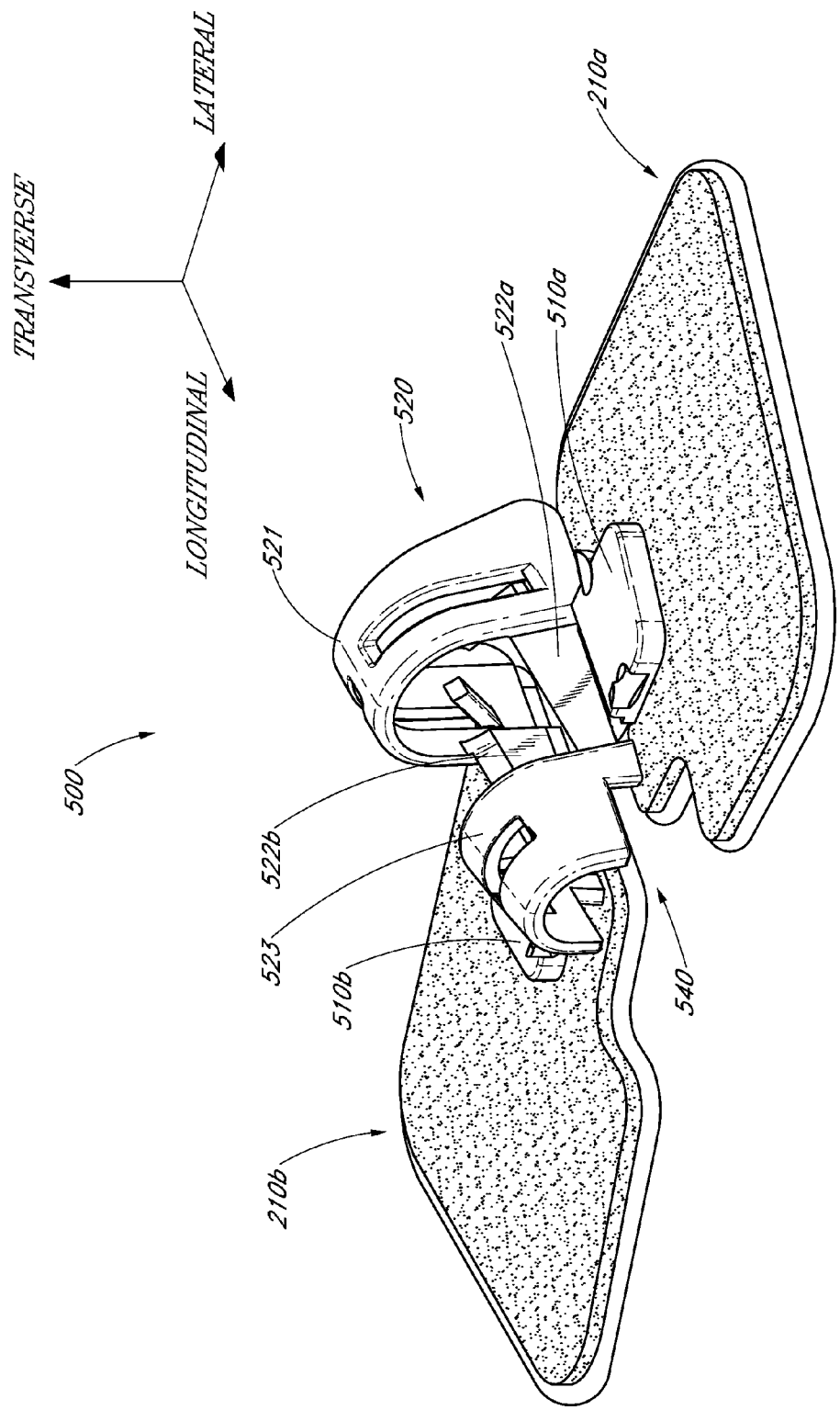
FIG. 16 is a front perspective view of a securement device, including a retainer and anchor pads, in accordance with another preferred embodiment of the present invention.

To assist in the description of the components of the securement devices, the following coordinate terms are used, consistent with the coordinate axes illustrated in FIGS. 1 and 16. A "longitudinal axis" is generally parallel to the channel of the retainer. A "lateral axis" is normal to the longitudinal axis and is generally parallel to the plane of the anchor pads. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body, as will be understood by one of skill in the art. The terms "upper," "lower," "top," "bottom," "underside," "upperside" and the like, which are used to describe the present securement devices, are used in reference to the illustrated orientation of the embodiments. For example, the term "upperside" is used to describe the portion of the retainer that is located above a lateral axis that passes through the axis of the channel. The term "underside" is used to describe the portion of the retainer that is located below a lateral axis that passes through the axis of the channel. Brief introductions to some of the features, which are common to the described embodiments of the securement devices, are now described.

The preferred embodiments of the present invention advantageously provide a securement device for securing one or more medical articles to a patient. The medical article preferably has an elongated body. The elongated body cooperates with a retainer to arrest movement of the medical article, for example, in longitudinal, lateral, and transverse directions when placed within the retainer.

In each of the embodiments described below, the retainer has a channel extending therethrough. The channel has a longitudinal access opening located on an underside of the retainer to allow ingress or egress of the medical article. The medical article is installed or removed from the underside of the retainer via this access opening. Thus, the retainer may be placed over the top of the medical article and/or the medical article may be placed through the bottom of the retainer. Such an arrangement allows the medical provider to align at least a portion of the medical article with the retainer prior to fixing the retainer to the patient's skin.

The retainer includes at least one retention surface that cooperates with at least one contact point or surface on the medical article. The one or more retention surfaces can engage at least one contact surface on the medical article so as to inhibit transverse and/or lateral movement of the medical article relative to the retainer. For example, the retention surfaces can be formed on one or more retention members extending into the channel. The retention surfaces can be shaped so as to contact a downward facing surface and/or lateral facing surface such that relative transverse movement and/or lateral movement of the medical article is arrested. In some embodiments, a retention surface can include a plurality of surfaces separated by one or more contours. For example, a retention surface can include an upper facing surface and a surface that extends at an angle relative to the upper facing surface so as to arrest transverse and longitudinal movement of the medical article relative to the retainer.

The retainer may include multiple retention members with each retention member having the same length. Alternatively, one or more of the retention members may have a different length than one or more other retention members. By having retention members with different lengths, their retention surfaces can contact different sized medical articles. For example, a longer retention member may contact a medical article that has a smaller diameter while a shorter retention member may contact a medical article that has a larger diameter.

The retainer may also include at least one abutment (preferably an abutment surface) that cooperates with at least one contact point or surface on the medical article. The one or more abutments of the retainer extend generally normal to the axis of the channel and can be, for example, but without limitation a portion of a retention member, a surface, a wall of a slot, a ridge, a pill, a protuberance, or like structures. The abutment cooperates with the one or more contact points or surfaces of the medical article to inhibit longitudinal movement of the medical article through the channel. For example, the abutment could be a surface on a retention member that extends into the channel which acts against at least a portion of an outwardly extending member of the medical article so as to inhibit longitudinal movement of the medical article in the distal direction. Additionally, the abutment could be a distal facing surface on the retainer that acts against the outwardly extending member of the medical article to inhibit longitudinal movement in the proximal direction. In this way, the medical article can be limited in its proximal movement (i.e., movement toward the patient) and in its distal movement (i.e., movement away from the patient) once the medical article contacts or abuts at least one abutment of the retainer. The outwardly extending member extends away from the medical article. For example, the outwardly extending member can extend in a radial direction from the medical article.

The retainer of each embodiment described below further includes at least one support that is preferably disposed on the underside of the retainer at a position lower than the access opening. Preferably, the retainer holds the retained portion of medical article away from the patient's skin, when the retained portion is positioned within the retainer channel, to avoid chaffing or excoriating the skin. The support in each of the illustrated embodiments includes left and right mounting wings that are integral with the body member and are attached to left and right anchor pads. The lower surfaces of the left and right anchor pads attach to the patient's skin.

The retainer and anchor pads also can have other constructions in order to inhibit contact between the skin and the retainer, as well as between the skin and the retained portion of the medical article. For example, the anchor pads can be thicker, in which case the mounting wings can be located higher on the retainer body.

To facilitate a complete understanding of the disclosed embodiments, the remainder of the detailed description describes the securement device with reference to the figures, wherein like elements may be referenced with like numerals throughout the following description.

Figure 2:
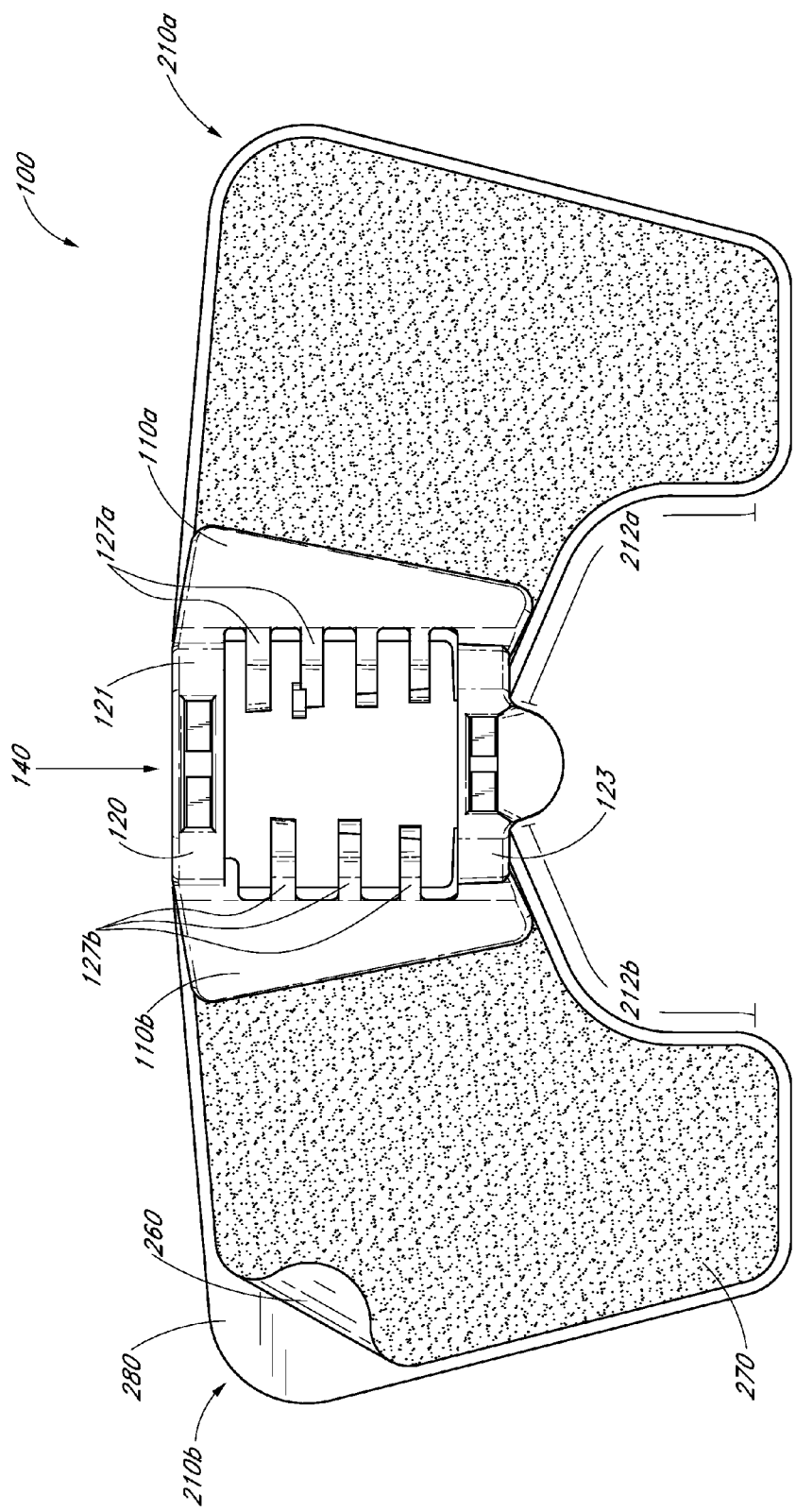
FIG. 2 is a top plan view of the securement device of FIG. 1.

FIG. 1 is a perspective view of a securement device 100 configured in accordance with an embodiment of the present invention. FIG. 2 is a top plan view of the securement device 100 of FIG. 1. As shown in FIGS. 1 and 2, the illustrated securement device 100 includes three main components, two anchor pads 210a, 210b and a retainer 120. The illustrated retainer 120 includes a right mounting wing or support 110a and a left mounting wing or support 110b. Each support 110 is disposed upon the respective one of the anchor pads 210a, 210b. The supports 110a, 110b extend generally in a lateral direction away from a center of the retainer 120.

The retainer 120 further includes a body member. The body member of the retainer 120 illustrated in FIG. 1 includes a proximal portion 123 and a distal portion 121. The supports 110a, 110b are fixed relative to the proximal portion 123 and the distal portion 121. The proximal portion 123 and the distal portion 121 at least partially define a channel 140 that extends through the retainer 120. The retainer also includes one or more first retention members 127a and one or more second retention members 127b. In the illustrated embodiment the retainer 120 includes a first set of retention members 127a and a second set of retention members 127b.

The first and second sets of retentions members 127a, 127b extend into the channel 140 from opposite lateral sides. Each retention member 127 includes a secured end which is coupled to a support 110 and an unsecured distal end which extends into the channel 140. In this way, each retention member 127 is cantilevered with respect to the support 110 from which it extends. The unsecured ends of the retention members 127 can deflect, flex, or otherwise move relative to the supports 110 from which they extend and relative to the unsecured ends of the other retention members.

The retention members 127 may have the same length. Alternatively, one or more of the retention members 127 may have a different length than one or more other retention members 127. By having retention members 127 with different lengths, their distal ends can contact different sized medical articles. For example, a longer retention member 127 may contact a medical article that has a smaller diameter while a shorter retention member 127 may contact a medical article that has a larger diameter.

The retainer 120 can include a generally rigid structure (at least in comparison to foam or tape). However, the retainer 120 can also be somewhat flexible in nature, due both in part to its structure and to the material(s) used to form the retainer 120. Suitably rigid but flexible materials include, for example, but without limitation: plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. However, other materials can be utilized.

The proximal portion 123, distal portion 121, and mounting wings 110a, 110b preferably are integrally formed to comprise a unitary retainer. This can be accomplished in any of a variety of ways well known to those skilled in the art. For instance, the entire retainer can be injection molded in order to reduce fabrication costs. The illustrated retainer 120 preferably is formed by injection molding using polyethylene or polypropylene material. The retainer, however, can comprise a non-unitary structure. In this manner, the proximal portion 123, the distal portion 121, and/or one or both of the mounting wings 110a, 110b is formed separately and then coupled together.

The retainer 120 is attached to the upper surface 270 of the anchor pad 210 via the mounting wings 110a, 110b, as is shown in FIG. 2. The retainer 120 is desirably secured to the upper surface of the pad 210 by a solvent bond adhesive, such as cyanoacrylate or other bonding material. One such adhesive is available commercially as Part No. 4693 from 3M.

When the anchor pads 210 are secured to the skin of the patient, the medical article is inhibited from moving substantially in either the lateral or transverse directions relative to the patient. Such movement may be inhibited by contact between at least one retention surface on the retainer 120 and the medical article. The distal and proximal portions 121, 123 and the retention members 127 can include retentions surfaces for arresting lateral and/or transverse movement of the medical article.

Further, longitudinal movement of the medical article is inhibited by engagement between at least one abutment surface on the retainer 120 and a contact surface or mating surface on the medical article. The abutment surface on the retainer 120 preferably extends generally normal to the axis of the channel 140. The abutment surface can be located at or between the distal and proximal portions 121, 123 of the retainer 120. For example, the abutment surface or feature can be a surface of the retention member 127.

Additionally, the retainer 120 can include an abutment surface located on the distal and/or proximal portions 121, 123 of the retainer. For example, a distal facing surface of the proximal portion 123 can abut the medical article so as to prevent or inhibit proximal movement of the medical article and/or a proximal facing surface of the distal portion 121 can abut the medical article so as to prevent or inhibit distal movement of the medical article. In some embodiments, the distal and proximal portions 121, 123 are spaced from one another so as to receive an outwardly extending member of the medical article, e.g., a spin nut, therebetween and to abut opposite sides of the outwardly extending member to inhibit longitudinal movement of the medical article relative to the retainer 120.

As noted above, the securement device 100 can form a component of a catheterization system that also includes one or more medical articles, such as connector fittings, catheters, hubs, catheter adaptors, fluid supply lines, or other articles suitable for securement via the anchor pads and retainer. A longitudinal access opening in the retainer 120 is aligned with the medical article. The medical article is inserted through the opening and between the first and second sets of retention members 127a, 127b into the channel 140 of the retainer 120. The anchor pads 210a, 210b are then secured to the skin of the patient, generally by an adhesive disposed upon the bottom surface of the pads. In this way, the retainer 120 secures the medical article to the patient. Thus, the retainer at least restricts, if not prevents, lateral, transverse, and/or longitudinal movement of the retained section of the medical article. The embodiment illustrated is preferably for use with a catheter hub and connector fitting which together form part of a medical article as described with reference to FIGS. 12 through 15. The embodiments of the anchor pad and the retainer are described in more detail below.

Anchor Pad

As shown in FIG. 2, the general structure of each anchor pad 210a, 210b comprises a generally rectangular shape with a scalloped region 212a, 212b located at a corner of each anchor pad. The scalloped configuration eases the process of aligning the securement device 100 with a catheter insertion site in the patient's skin. Although only a single shape of the anchor pad is illustrated in FIGS. 1, 2, and 12 through 15, those of skill in the art will recognize that a variety of shapes can be used.

Each anchor pad 210 desirably comprises a laminate structure with an upper plastic, paper or foam layer (e.g., closed-cell polyethylene foam) and a lower adhesive layer. The lower adhesive layer constitutes a lower surface 260 of the anchor pad. The lower surface 260 desirably is cover by a medical-grade adhesive and can be either diaphoretic or nondiaphoretic, depending upon the particular application. Such foam with an adhesive layer is available commercially from Avery Dennison of Painsville, Ohio. While not illustrated, the anchor pads 210a, 210b can include suture holes in addition to the adhesive layer to further secure the anchor pad to the patient's skin.

In other variations, a hydrocolloid adhesive or zinc oxide-based adhesive can advantageously be used upon the anchor pads 210a, 210b for attaching the anchor pads to the skin of the patient. The hydrocolloid or zinc oxide-based adhesive can be used either alone or in combination with another medical grade adhesive (e.g., in combination with the adhesive available from Avery Dennison). Hydrocolloid and zinc oxide-based adhesives have less of a tendency to excoriate the skin of a patient when removed. This can be particularly important for patients whose skin is more sensitive or fragile, such as neonates and those with a collagen deficiency or other skin related condition.

In another variation, each anchor pad 210a, 210b comprises a laminate structure with an upper woven layer and a lower adhesive layer. The upper layer can be polyester or other suitable polymer or textile materials. One particular suitable material is woven polyester available commercially under the name "Tricot" from Tyco. The lower adhesive layer constitutes the lower surface 260 of the anchor pad. The lower surface desirably is a medical-grade adhesive and can be either diaphoretic or nondiaphoretic, depending upon the particular application.

A surface of the upper foam layer constitutes an upper surface 270 of the anchor pads 210a, 210b. The upper surface 270 can be roughened by corona-treating the foam with a low electric charge. The roughened or porous upper surface can improve the quality of the adhesive joint (which is described below) between the mounting wings 110 and the anchor pads 210. In a further variation, the flexible anchor pad can comprise an upper paper or other woven or nonwoven cloth or plastic layer in lieu of a roughened upper foam surface.

The anchor pads 210a, 210b preferably are arranged with respect to the retainer 120 such that the tip of the medical article does not extend beyond the front edge of the mounting wings 110 when the medical article is properly inserted within the retainer 120. The healthcare provider can be instructed to generally align the medical article tip with the front edges of the anchor pads 210a, 210b before inserting the medical article into the retainer 120.

As illustrated in FIG. 2, a removable paper or plastic release liner 280 desirably covers the adhesive lower surface 260 before use. The liner 280 preferably resists tearing and desirably is divided into a plurality of pieces to ease attachment of the pad to a patient's skin.

The liner 280 can include a folded over portion to define a pull tab. The pull tab can be utilized to remove the paper or plastic release liner 280 from the adhesive lower surface 260 before use. A healthcare provider uses the pull tab by grasping and pulling on it so that the liner 280 is separated from the lower surface 260. The pull tab overcomes any requirement that the healthcare provider pick at a corner edge or other segment of the liner in order to separate the liner from the adhesive layer.

The pull tab, of course, can be designed in a variety of configurations. For example, the pull tab can be located along a center line of the anchor pad 210; or alternatively, the pull tab can be located along any line of the anchor pad 210 in order to ease the application of the anchor pad onto the patient's skin at a specific site. For example, an area of a patient's skin with an abrupt bend, such as at a joint, can require that the pull tab be aligned toward one of the lateral ends of the anchor pad 210 rather than along the center line.

Retainer

Figure 3:
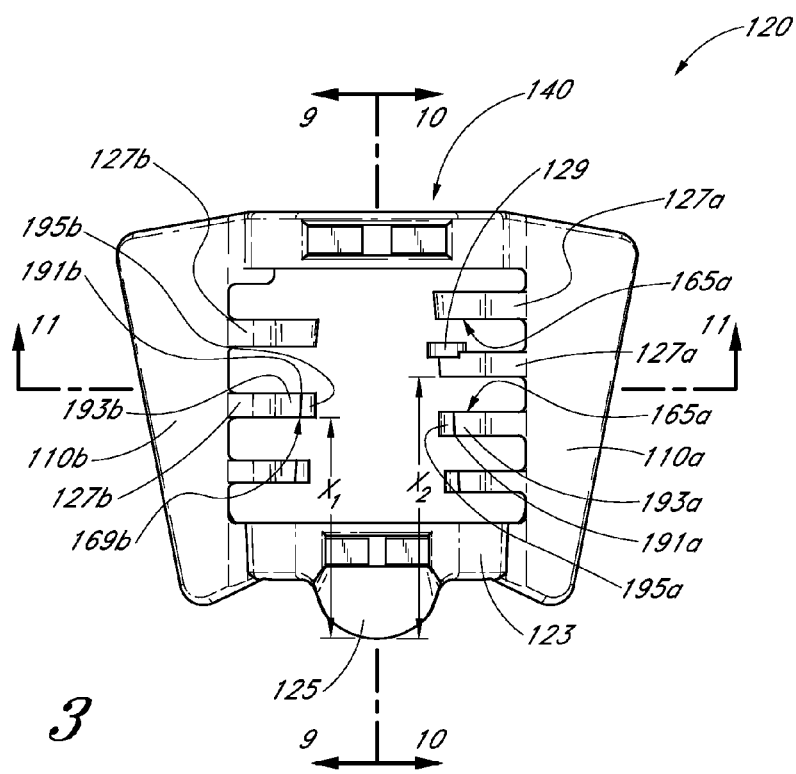
FIG. 3 is a top plan view of the retainer from FIG. 2.
Figure 4:
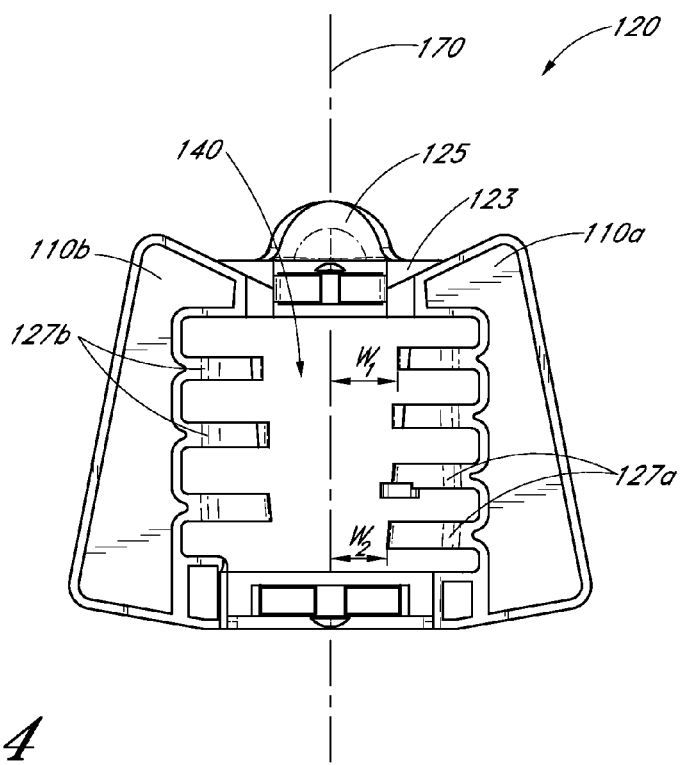
FIG. 4 is a bottom plan view of the retainer of FIG. 3.

An embodiment of the retainer 120 is now described with reference to FIGS. 3 through 11. FIG. 3 is a top plan view of the retainer 120. FIG. 4 is a bottom plan view of the retainer 120. As shown in FIGS. 3 and 4, the retainer 120 is elongated in the longitudinal direction so as to at least partially define the channel 140 extending between the proximal portion 123, and the distal portion 121. The channel 140 extends through the retainer 120 in a longitudinal direction for receiving a section of a medical article, e.g., a connector fitting.

The channel 140 is capable of receiving a portion or length of the medical article and is generally configured to house this portion of the medical article. Additionally, as discussed below, effective securement of the medical article relative to the retainer 120 can be achieved by the abutment of the retention members 127 with one or more contact surfaces on the medical article and/or engagement between one or more retention surfaces and the medical article. Each abutment surface or retention surface can cooperate with a contact surface on the medical article to inhibit movement of the medical article relative to the retainer 120. Additionally, securement can be achieved by the placement of the medical article between retention surfaces of the retention members and retention surfaces of the downwardly extending fingers to grip the medical article therebetween.

Figure 5:
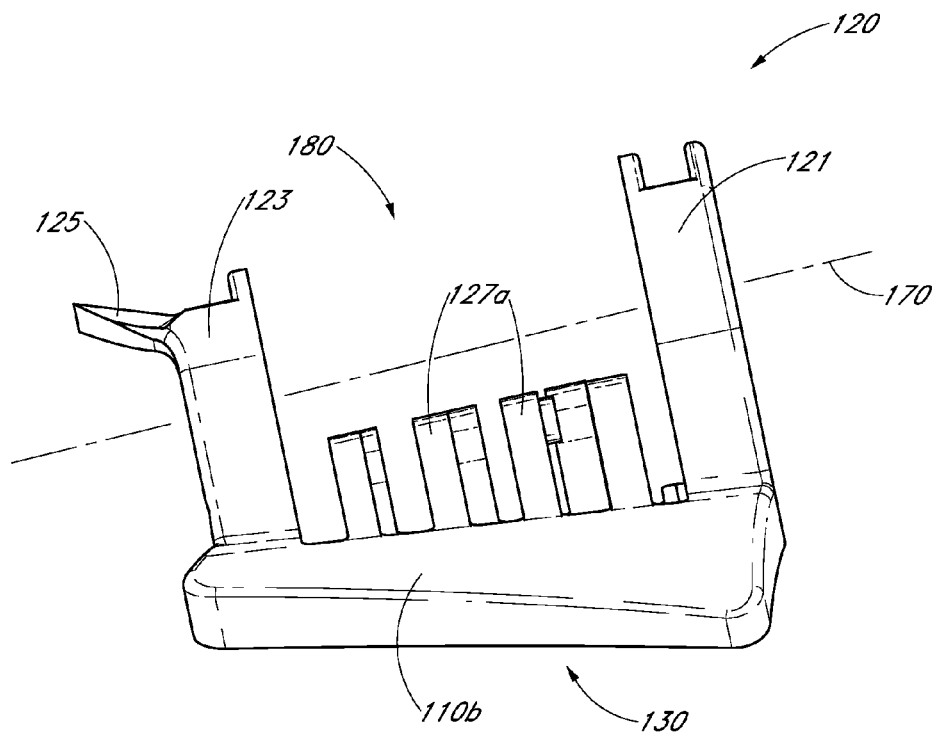
FIG. 5 is a right side elevational view of the retainer of FIG. 3.
Figure 6:
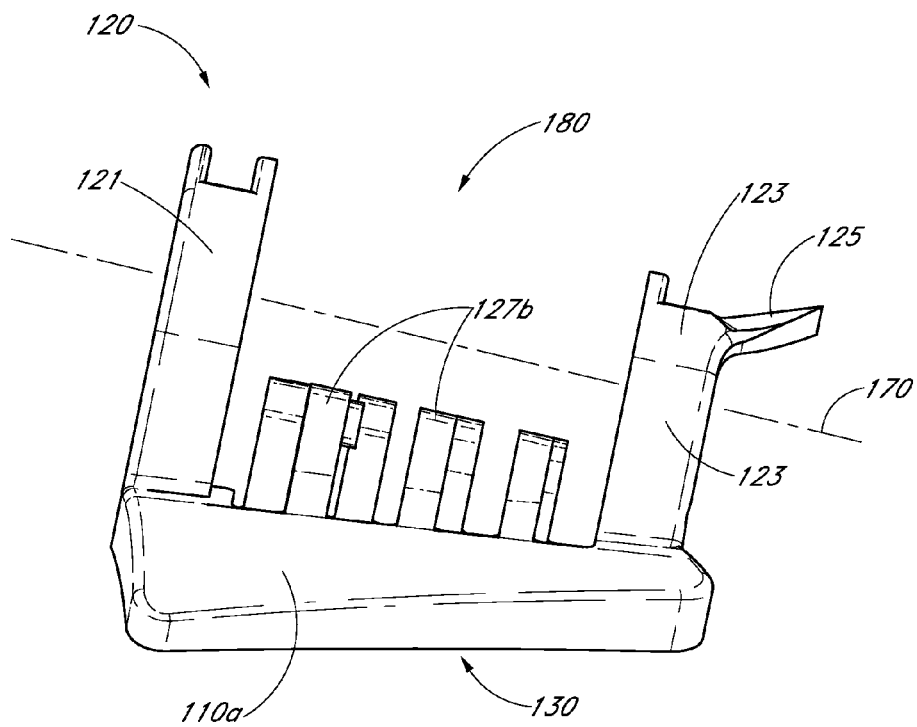
FIG. 6 is a left side elevational view of the retainer of FIG. 3.

In the illustrated embodiment (see FIGS. 5 through 8), the channel 140 has a generally semi-circular cross-sectional shape. The cross-sectional shape of the channel 140 can be selected depending on the geometry of the portion of the medical article to be retained. For example, in a retainer 120 that is configured to retain a portion of a medical article having a constant outer diameter, the channel 140 preferably has a constant radius along its length. In contrast, as illustrated in FIGS. 5 and 6, the proximal portion 123 of the retainer 120 defines a smaller portion of the channel 140 than the distal portion 121. Thus, in the illustrated embodiment, the channel 140 has at least two sections with different radii. In this way, the size and shape of the channel 140 can be chosen to match or to approximate the size and shape of the medical article or portion thereof, e.g., the catheter hub and/or connector fitting, to be retained. By matching the size and shape of at least a portion of the channel 140 to the outer surface of the secured portion of a medical article, a more effective securement may be achieved.

Although the channel 140 can be formed in various shapes depending upon the desired application (e.g., depending upon a shape of the retained portion of the medical article for which the retainer is designed to be used), it is advantageous for the longitudinal dimension of the channel 140 defined by the retainer 120 to be sufficiently long to provide stability to the retained portion of the medical article along its length. That is, the retainer 120 receives a sufficient length of the medical article to inhibit movement of the medical article in the lateral, longitudinal and transverse direction (i.e., to inhibit yaw, pitch and axial movement of the article). Also, the lateral dimensions of the proximal and distal portions 123, 121 of the retainer 120 desirably allow the healthcare provider to easily and naturally grip the retainer using a gloved hand.

With continued reference to FIGS. 3 and 4, the retention members 127 extend into the channel 140 from at least one of the lateral sides of the channel. The unsecured end of each retention member 127 can include a retention surface 165 for contacting a portion of the medical article. The sizes, shapes, and orientations of the retention surfaces 165 can vary from retention member to retention member. For example, a retention surface 165a on a more distal retention member 127a can include a single surface while a retention surface 165a on a more proximal retention member 127a can include multiple surfaces that form its retention surface. The more proximal retention surface 165 can include an upper facing surface 195a and a surface 193a that is angled relative to the upper facing surface 195a. The two surfaces 195a, 193a can be separated by a contour or edge 191a. In this way, the sizes, shapes, and orientations of the retention surfaces 165 can be selected to provide support for an intended contact surface on the medical article. For example, a more distal retention surface 165a may contact a point of the medical article that is higher than a point of contact for a more proximal retention surface 165a. As a result, the more proximal retention surface 165a can be configured to provide additional transverse support to the medical article then the more distal retention surface 165a while the more distal retention surface is configured to provide more lateral support to the medical article than the more proximal retention surface.

As illustrated, the retainer 120 includes a first set of retention members 127a extending into the channel 140 from a first side and a second set of retention members 127b extending into the channel from a second side. One or more of the retention members 127a can be spaced apart in the longitudinal direction from other retention members 127a so as to form slots, gaps, or spaces therebetween. Similarly, one or more of the retention members 127b can be spaced apart in the longitudinal direction from other retention members 127b so as to form slots, gaps, or spaces therebetween.

In some embodiments, the first set of retention member 127a and the second set of retention members 127b are staggered laterally along the channel axis such that the lateral sides of the retainer 120 are asymmetric. That is to say, each retention member 127 defines a different longitudinal length between a proximal end of the retainer 120 and the retention member. For example, as shown in FIG. 3, $X_1$ and $X_2$ illustrate different longitudinal lengths between the proximal end of the retainer 120 and two of the retention members 127. In this way, each retention member can engage a different contact surface on a received portion of the medical article. Additionally, this configuration allows the retainer 120 to accommodate connector fittings having different longitudinal lengths as described with reference to FIGS. 14 and 15. For example, in use, a proximal facing surface of at least one of the retention members 127 can abut a distal facing surface of a medical article, e.g., a distal end of a connector fitting, such that longitudinal movement of the medical article in the distal direction is inhibited while another retention surface of the retention members 127 can contact the medical article so as to inhibit lateral and transverse movement of the medical article. Further, the asymmetric appearance of the retainer may be pleasing to the eye in combination with the sculpted outer profile of the anchor pads.

As illustrated in FIG. 4, the lateral distance that the engagement members 127 extend into the channel 140 toward the axis 170 of the channel can vary from engagement member to engagement member. For example, a first distance or width $W_1$ measured between the proximal-most engagement member 127a and the channel axis 170 can be greater than a second distance or width $W_2$ measured between the distal-most engagement member 127a and the channel axis. Widths $W_1$ and $W_2$ can be selected so as to provide more clearance within the channel 140 at a proximal section of the channel than at a distal section.

In some embodiments, the retainer 120 includes an abutment feature 129 or pill. For example, one or more of the retention members 127 can include one or more abutment features 129. The abutment feature 129 is configured to abut or contact a surface of a medical article, depending on the size of the medical article, to inhibit or prevent movement of the medical article in at least one direction relative to the retainer 120. For example, the abutment feature 129 illustrated in FIG. 3 is disposed on the distal end of a retention member 127 and extends normal to the channel axis. The abutment feature 129 illustrated in FIG. 3 at least inhibits movement of a medical article 120 that is sized to contact the abutment feature 129 in a longitudinal direction away from the patient. The retainer 120 may include multiple abutment features 129 or pills spaced along the longitudinal axis with each abutment feature 129 being configured to contact different surfaces of a single medical article or the same surface (e.g., spin nut) of different sized medical articles 120.

The abutment feature 129 can be configured to abut a distal or proximal facing surface of a medical article to inhibit longitudinal movement of the medical article relative to the retainer 120. In some embodiments, the size, shape, and location of the abutment 29 is selected based at least in part on the medical article to be secured by the retainer 120. For example, the abutment feature 129 can be sized and shaped so as to abut a distal facing surface of a spin nut between an outer edge of the distal facing surface and the medical line disposed near the inner edge of the distal facing surface.

FIGS. 5 and 6 are side views of the retainer 120. As illustrated, an axis 170 of the channel 140 lies at an angle with respect to the base surfaces 130 of the mounting wings 110. The desired angle between the medical article and the patient is created by angling the axis 170 of the channel 140. This angle is selected in order to align the axis 170 of the channel 140 of the retainer with the desired incident angle with which the medical article is to contact the skin of the patient. A variety of different angles can be used, ranging from 0° to 45°, and more preferably from 5° to 25°. For instance, for the securement of intravenous catheters, it is desirable for the angle of incidence of the catheter to the skin of the patient to be between about 7° to about 15°. For the securement of arterial catheters, it is desirable for the angle of incident of the catheter to the skin of the patient to be about 12.5°. By angling the axis 170 of the channel 140 at the desired angle, which will depend upon the particular securement application (e.g., securing an arterial catheter, an intravenous catheter, etc.), the proper angle of incidence for a catheter can be maintained.

The angle with which the medical article is to contact the skin of the patient can also be controlled by the angle of the transverse dimensions of the retention members 127. As one or more of the retention members 127 can contact a surface of the medical article so as to provide support thereto, the retention members can be dimensioned to support the medical article in a desired position within the channel 140. For example, the maximum transverse dimensions of the retention members 127 can increase from the proximal direction to the distal direction. That is to say, the most distal retention member 127b can have a greater transverse dimension than the most proximal retention member 127b such that the retention surface of the most distal retention member supports the medical article higher above the patient's skin than the most proximal retention member. In this way, the retention members 127 can support the medical article along the axis 170 of the channel.

In the illustrated embodiment, the retainer 120 includes an access window or opening 180 disposed between the proximal portion 123 and the distal portion 121. This opening 180 allows the healthcare provider to access a retained portion of the medical article secured by the retainer. For example, the healthcare provider may utilize the opening 180 to grip a connector fitting received within the retainer 120. Additionally, the healthcare provider may view the medical article through the opening 180 between the proximal portion 123 and the distal portion 121 to verify fluid flow and/or flashback. In some embodiments, a portion of the medical article may pass through the opening 180 away from the retainer 120 when secured by the securement device 100. For example, an access port or tab can extend through the opening 180 away from the channel 140.

As shown in FIGS. 3 through 6, the retainer 120 includes a finger pad 125 that a healthcare provider can press down upon. The finger pad 125 may extend proximally from the proximal portion 125 and can include a depression for receiving a portion of a finger. In this way, the depression encourages the healthcare provider to utilize the finger pad 125 to grip or hold the retainer 120. Such a configuration can act to discourage the healthcare provider from gripping the proximal and/or distal portions 123, 121 on their lateral sides during use. Such a side grip could squeeze or constrict the retainer 120 and channel 140 making it harder to insert the medical article between the retention members 127. By pushing down on the retainer 120, this constrictive effect is avoided.

Figure 7:
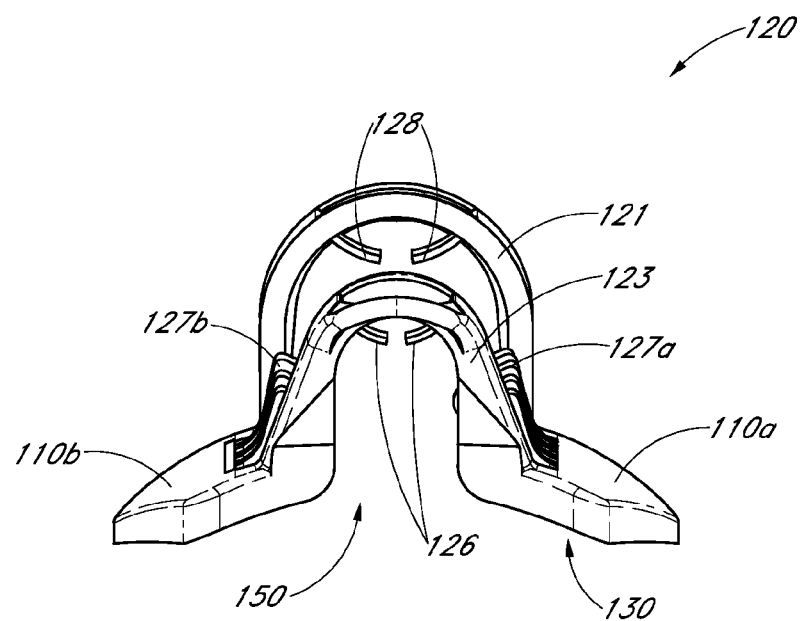
FIG. 7 is a front elevational view of the retainer of FIG. 3.
Figure 8:
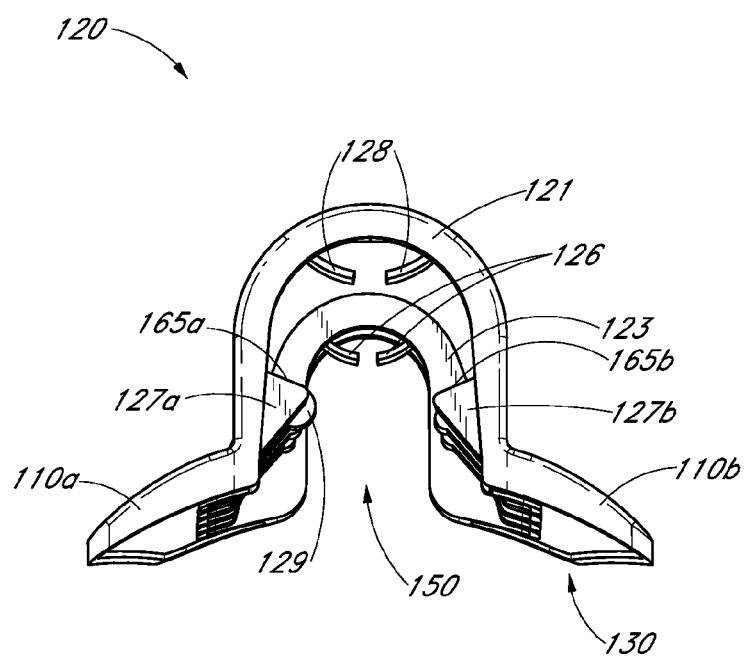
FIG. 8 is a rear elevational view of the retainer of FIG. 3.

As illustrated in FIGS. 7 and 8, the base surface 130 of the retainer 120 can have a concave curved shape when viewed from the front and rear sides. The degree of curvature can be varied depending on the expected location of usage or application of the securement device 100. It will be appreciated that many common sites for insertion of medical lines which require securement will be located on anatomical regions exhibiting convex curvature, such as a dorsal side of a hand, a arm, a leg, a contact surface, etc. By providing a concave bottom profile to the retainer 120, the retainer will rock less once placed upon the patient via the anchor pads 210a, 210b.

As shown most clearly in FIGS. 7 and 8, the lower side of the retainer 120 includes an access or lower opening 150. The lower opening 150 may include contouring (e.g., chamfers) along its periphery in order to guide the medical article into the channel 140 when inserting the medical article into the retainer 120. For example, the lower opening 150 may include a chamfer between the right mounting wing 110a and the proximal portion 123 and/or between the right mounting wing 110a and the distal portion 121.

As is also illustrated in FIGS. 7 and 8, the retention surfaces 165 of each retention member 127 are disposed on an upper facing portion of the retention member 127. As discussed above, the retention surfaces 165 can act to support at least a portion of the retainer medical article within the channel 140 and hence away from the patient's skin. In some embodiments, the retention surfaces 165 can be shaped so as to match the portion of the medical article that contacts the retention surfaces. In this way, the retention surfaces 165 can be shaped to at least partially grip the received portion of the medical article. In some embodiments, the retention surfaces 165 are the only point of contact between the retention members 127 and the medical article when the medical article is secured in retainer 120. That is to say, the medical article need not contact any other portion of the retention members 127 other than the retention surface 165 when secured within the retainer 120. In some embodiments, the retention members 127 can include an adhesive. The adhesive can be located on the retention surfaces 165 so as to contact the received portion of the medical article and inhibit movement of the medical article relative to the retainer 120. Additionally or alternatively, the adhesive can be located on the abutment feature 129.

Figure 11:
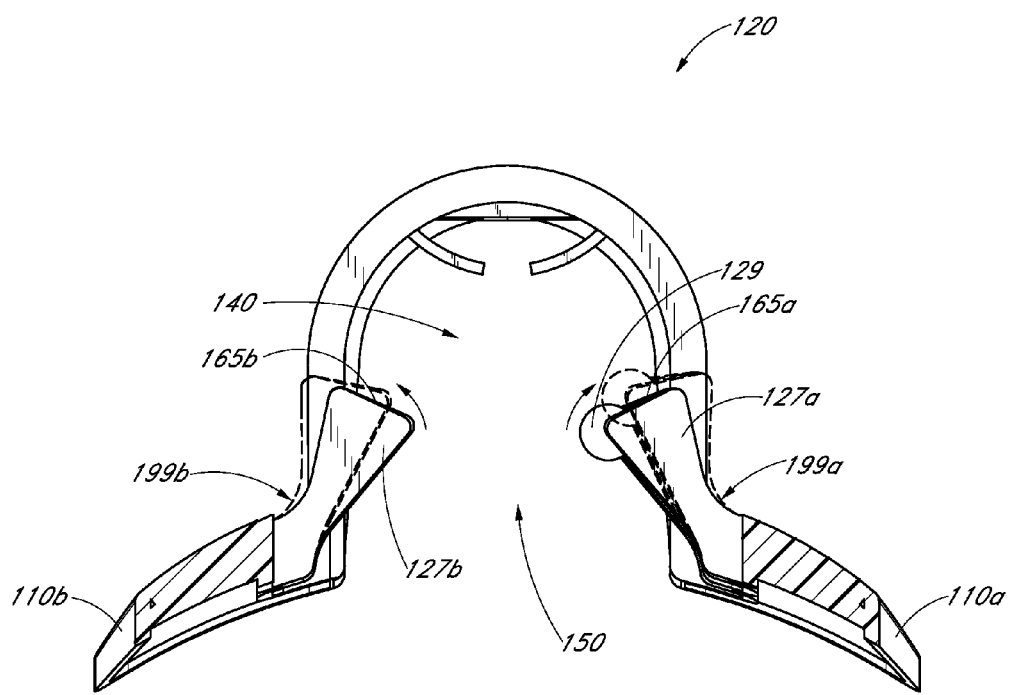
FIG. 11 is a cross-sectional view of the retainer taken along line 11-11 of FIG. 3.

As shown by dashed lines in FIG. 11, the unsecured ends of the retention members 127 may be flexible relative to the rest of the retainer 120. For example, the unsecured end of each of the retention members 127 may deflect, rotate, or otherwise move away from the channel axis when one or more contact forces are applied to the retention members. Additionally, the unsecured end of each retention member 127 may be deflected or otherwise move relative to the unsecured ends of the other retention members. Thus, the unsecured ends of the first set of retention members 127a may be deflected laterally away from the unsecured ends of the second set of retention members 127b and vice versa. In this way, a medical article inserted into the channel through the opening 150 may contact the retention members 127 and deflect them away from the channel axis to a deflected position (denoted by dashed lines).

The deflection of the unsecured ends of the retention members 127 can be facilitated by changing the profile of the retention member 127 in a region 199 disposed near the secured end. For example, the retention member 127 may be thinned in the region 199 relative to the rest of the retention member 127 such that the retention member may flex, deflect, or move about the region 199. In this way, the region 199 can act as a living hinge between the retention member 127 and the support 110 from which it extends. Such deflection widens the axis to the channel and allows the medical article to be inserted through the retention members 127 into a secured position.

Figure 9:
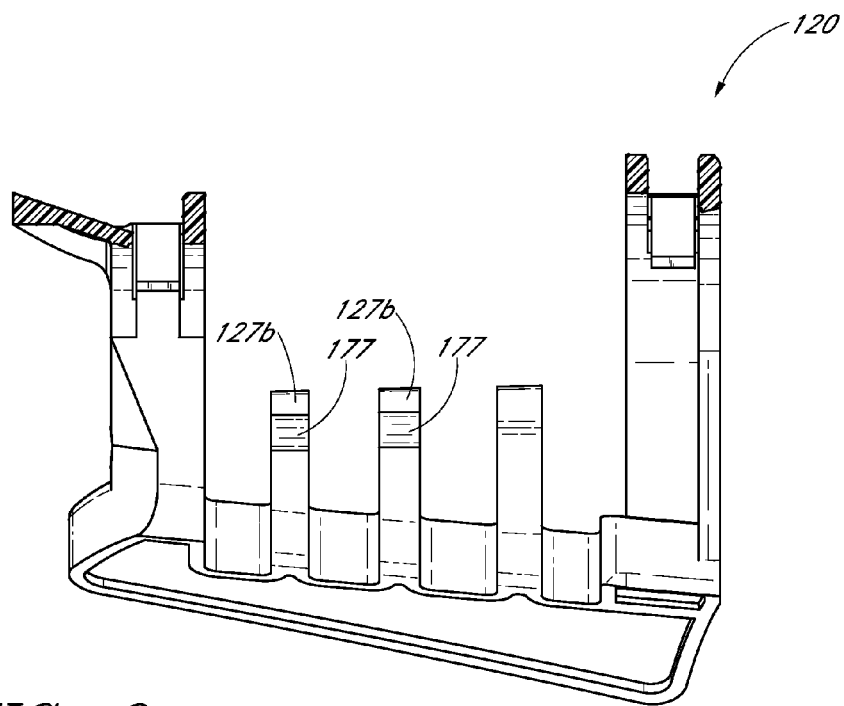
FIG. 9 is a cross-sectional view of the retainer taken along line 9-9 of FIG. 3.
Figure 10:
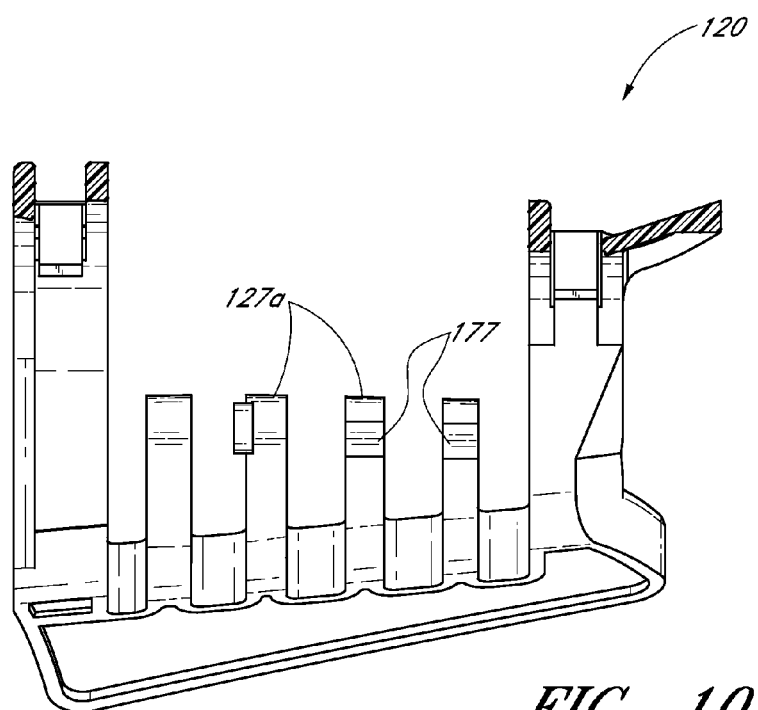
FIG. 10 is a cross-sectional view of the retainer taken along line 10-10 of FIG. 3.

As shown in FIGS. 9 and 10, in some embodiments, the retention members 127 can include a chamfered or curved corner 177. The profile of the corner 177 may be selected to match the portion of the medical article which contacts the corner 177. For example, the rounded surfaces 177 may have internal radii that match a radius of a received portion of the medical article that contacts the retention members 127.

In some embodiments, the retention members 127 are formed such that they are biased toward the un-deflected position (denoted in FIG. 11 by solid lines). Accordingly, after the received portion of the medical article has passed beyond the retention members 127 into the channel 140, the retention members returns to an un-deflected configuration such that retention surfaces 165 contact a downward and/or lateral facing surface of the medical article. For example, the retention surfaces 165 can contact a rounded surface located on a lower half of the medical article. In this way, the retention surfaces 165 act to support the medical article above the patient's skin and inhibit downward transverse movement and/or lateral movement of the medical article.

As shown in FIGS. 7 and 8, the retainer 120 can include one or more fingers 128 extending into the channel 140 from the distal portion 121. Also, the retainer can include one or more fingers 126 extending into the channel 140 from the proximal portion 123. The proximal and distal fingers 126, 128 include an unsecured end disposed within the channel 140 and a secured end coupled to the retainer. The fingers 126, 128 can contact an upper facing surface of the retained portion of the medical article so as to inhibit further upward transverse movement of the retained portion away from the patient's skin. In some embodiments, the fingers 126, 128 include retention surfaces disposed near the unsecured ends of the fingers for contacting the medical article.

In the illustrated embodiment, the retainer 120 includes a pair of fingers 128 extending into the channel 140 from the distal portion 121 and a pair of fingers 126 extending into the channel from the proximal portion 123. The distal fingers 128 are juxtaposed from one another across the channel axis and the proximal fingers 126 are juxtaposed from one another across the channel axis. In this way, the distal fingers 128 may each apply opposite lateral forces to a portion of the medical article contacted by the distal fingers 128. The proximal fingers 126 may each apply opposite lateral forces to another portion of the medical article in contact with the proximal fingers. Such opposing lateral forces may inhibit or restrict rotational movement of the medical article relative to the retainer.

The fingers 126, 128 may be configured as leaf springs so as to move between an extended configuration (see FIGS. 7 and 8) when not in contact with the medical article and a compressed configuration when the medical article contacts the fingers. When in the compressed configuration, the fingers 126, 128 may store potential energy and exert an opposing force on the medical article. The compressibility of the fingers 126, 128 allows the retainer 120 to accommodate medical articles having various radial dimensions. For example, a medical article with a first radial dimension may compress the fingers 126, 128 more than a medical article having a second radial dimension that is less than the first radial dimension. In this way, the fingers 126, 128 can act in concert to releasably grip and position the retained portion of the medical article within the channel 140. Thus, the medical article can be placed in position prior to attaching the securement device 100 to the patient without concern that the medical article will shift while the healthcare provider is attached the device 100 to the patient. Additionally, the compressibility of the fingers 126, 128 also permits the retained portion of the medical article to be readily released from the retainer 120. For example, the potential energy stored by the fingers 126, 128 may be utilized to bias the medical article away from the channel.

Medical Articles

Figure 12:
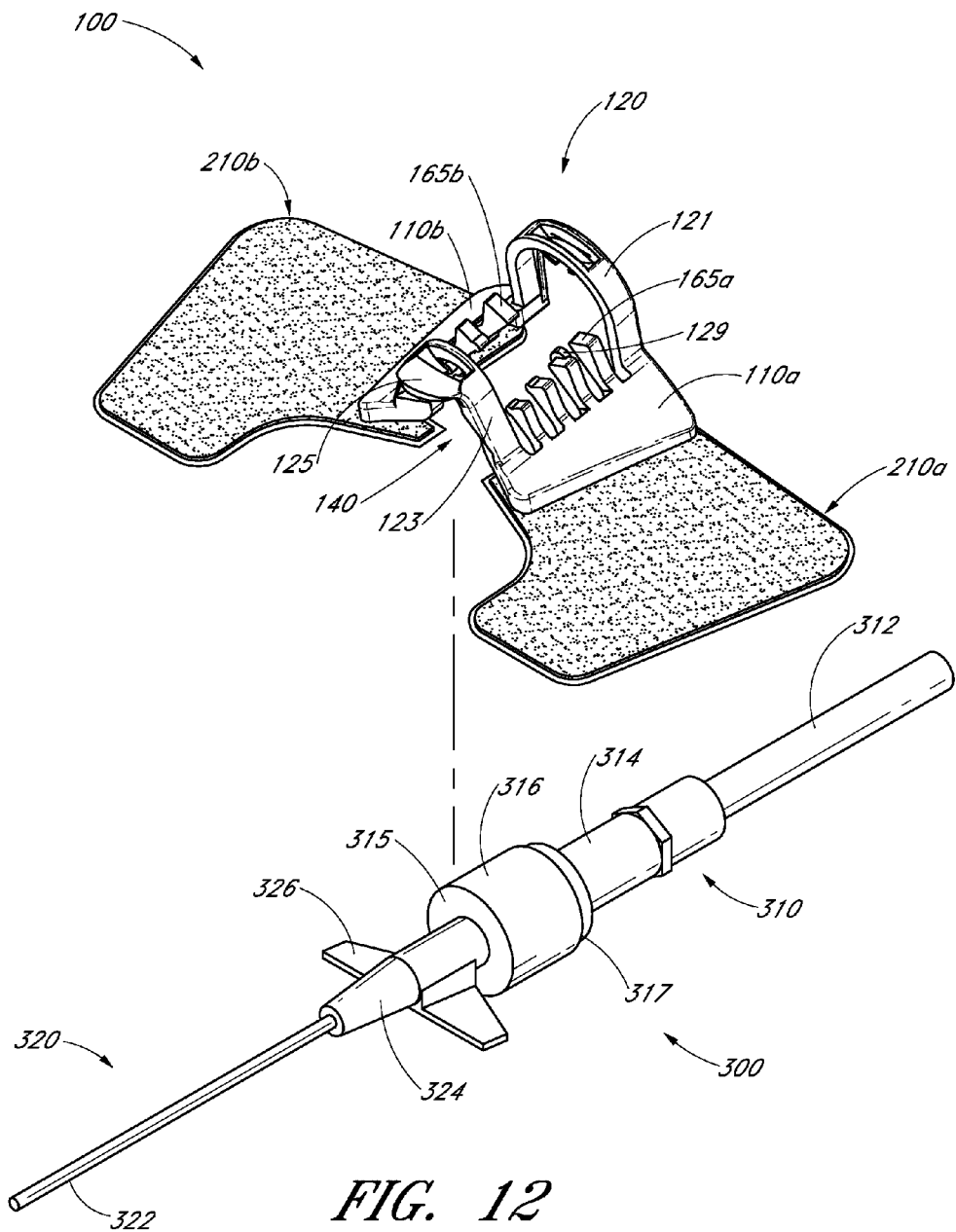
FIG. 12 is a perspective view of an exemplary medical article located below the securement device of FIG. 1 prior to insertion into the securement device.

An exemplary medical article for use with the embodiment of the securement device described above will now be described with reference to FIGS. 12 through 14. The medical article can be a single medical component or a combination of one or more medical components. Such medical components can be or include, for example, but without limitation, connector fittings, catheters, catheter hubs, catheter adaptors, fluid supply lines, or other similar articles. FIG. 12 is a perspective view of an exemplary medical article 300 located below the securement device 100 of FIG. 1 prior to insertion into the securement device. The medical article 300 includes a catheter 320 and a connector 310 forming a portion of a catheterization assembly. The catheter 320 includes a tubular member 322 for insertion into a patient's vasculature and a catheter hub 324 for connecting the tubular member 322 to a medical line. The catheter hub 324 can optionally include one or more stabilizing wings 326 extending laterally from the hub.

In some embodiments, the connector 310 includes a connector fitting 314 disposed upon the end of a medical line 312 which can be connected to a drip bag, blood monitor, or other fluid related medical apparatus. The connector 310 also includes a spin nut 316 disposed around the connector fitting 314 and extending radially from the lumen of the connector fitting. The spin nut 316 is substantially cylindrical in form and is able to move upon the connector fitting 314. The spin nut 316 is capable of both rotational motion around the axis of the connector fitting 314 and axial motion in both the proximal and distal directions along the length of the elongated body of the fitting. The spin nut 314 also includes internal screw threads. The catheter hub 324 includes an external screw thread near the distal end of the hub. The screw thread can be used in association with the spin nut 316 in order to securely interconnect the connector fitting 314 and the catheter hub 324. In this way, the lumen of the connector fitting 314 is disposed in fluid communication with the lumen of the catheter hub 324 providing fluid communication between the medical line 312 and the patient's vasculature.

As illustrated, the spin nut 316 has at least two contact surfaces extending normal to the lumen of the connector fitting 314. For example, the spin nut 316 includes a proximal facing contact surface 315 disposed at a proximal end of the spin nut and a distal facing contact surface 317 disposed at a distal end of the spin nut. As discussed below, the contact surfaces 315, 317 of the spin nut 316 can engage one or more abutments of the retainer 120 so as to limit longitudinal movement of the medical article 300 relative to the retainer. Similarly, in embodiments of medical articles comprising other outwardly extending members, such outwardly extending members can engage one or more abutments of the retainer 120 so as to limit longitudinal movement of the outwardly extending member relative to the retainer. Further, the retention surfaces 165 of the retention members 127 can support the medical article so that the medical article is elevated in the retainer 120 and such that the retained portion of the medical article 300 (e.g., the retained portion of the connector fitting 314) is raised from the patient's skin to lessen or eliminate compression, excoriation, and/or chaffing of the skin. Thus, the retainer 120 preferably lifts and holds the retained portion of the medical article 300 away from the patient's skin.

Method of Use

The following discussion of the method of use will be with reference to FIGS. 12 through 16, and will be in the context of intravenous catheterization. As the following discussion will illustrate, however, it is understood that the securement device 100 can be used in other catheterization procedures as well. The discussion of the method of use is intended to augment the above description, and thus, should be read together.

A healthcare provider preferably begins the procedure by inserting the tubular member or catheter needle 322 into a patient's vein in a known manner and then attaching the medical line 312 to the catheter needle 322 through the connector 310. In particular, the healthcare provider inserts the proximal end of the connector fitting 314 into the catheter hub 324 and then turns the spin nut 316 to thread the spin nut over the external thread at the distal end of the catheter hub 324. This action draws together the two medical article components and releasably interlocks them. The immediate connection of the medical line 312 to the catheter 320 inhibits a back flow of blood through the catheter. The healthcare provider now preferably secures the medical article 300 in place on the patient using the securement device 100. In some variations of this method, however, the securement device 100 is first attached to one or both of the medical article components (as well as the possibly to the patient) before the healthcare provider makes the connection between the connector 310 and the catheter 320.

FIG. 12 illustrates a perspective view of the medical article 300 with the connector 310 secured to the catheter 320. In this configuration, the medical article 300 can be aligned with the anchor pads 210a, 210b and the retainer 120. For example, the healthcare provider can align the channel 140 of the retainer 120 over the medical article 300 such that the spin nut 316 is disposed between the proximal portion 123 and the distal portion 121. As discussed above, to facilitate handling of the retainer 120 by the healthcare provider, the healthcare provider can place one or more fingers on the finger pad 125 to avoid a constrictive side grip.

From the position illustrated in FIG. 12, the healthcare provider guides the medical article 300 through the longitudinal access opening and into the channel 140 such that at least a portion of the medical article is disposed above the retention surfaces 165 of the retention members 127. Such placement may be accomplished by moving the medical article 300 relative to the retainer 120, by moving the retainer relative to the medical article, or by moving the retainer and the medical article relative to each other. To accomplish the proper placement of the medical article 300 within the retainer 120, the medical article may contact the lower facing surfaces of one or more retention members 127 so as to deflect these members away from the channel axis and provide a wider opening for the medical article to pass therethrough. In this way, the medical article 300 can slide along a lower facing surface of the retention members 127 until passing between the retention members 127.

Figure 13:
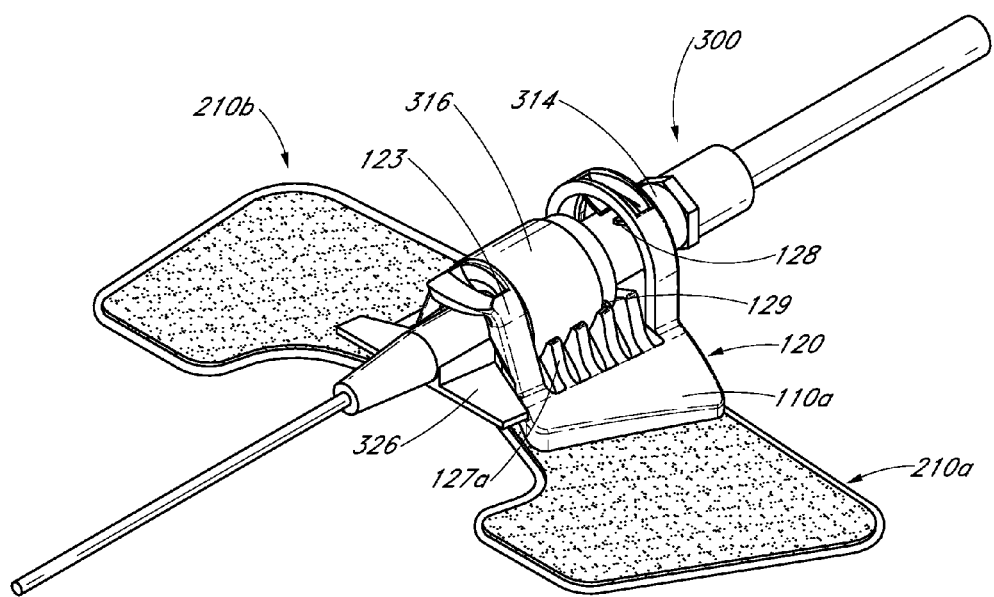
FIG. 13 is view similar to FIG. 12 except that the medical article is secured within the securement device.

FIG. 13 is a perspective view of the medical article 300 after the spin nut 316 has passed between the retention members 127 into the channel 140. In this position, the retention surfaces of the retention members 127 support the retainer portion of the medical article away from the supports 110. As described above, the retention surfaces can be sized and shaped so as to inhibit transverse and lateral movement of the spin nut 316 relative to the retainer 120. For example, the retention surfaces can be curved to generally match a contact surface on the spin nut 316. As illustrated, the distal fingers 128 engage an upper facing surface of the connector fitting. Additionally, the proximal fingers 126 engage an upper facing surface of the catheter hub 324. When the spin nut 316 is urged past the retention members 127, contact between the medical article 300 and the proximal fingers 126 and/or distal fingers 128 may compress the unsecured ends of the fingers away from the channel axis. Such compression may oppose the supporting forces applied by the retention members 127 so as to grip the medical article 300 therebetween. In this way, the medical article 300 can be secured relative to the patient's skin by the anchor pads 210a, 210b without the spin nut 316 contacting the patient.

Figure 14:
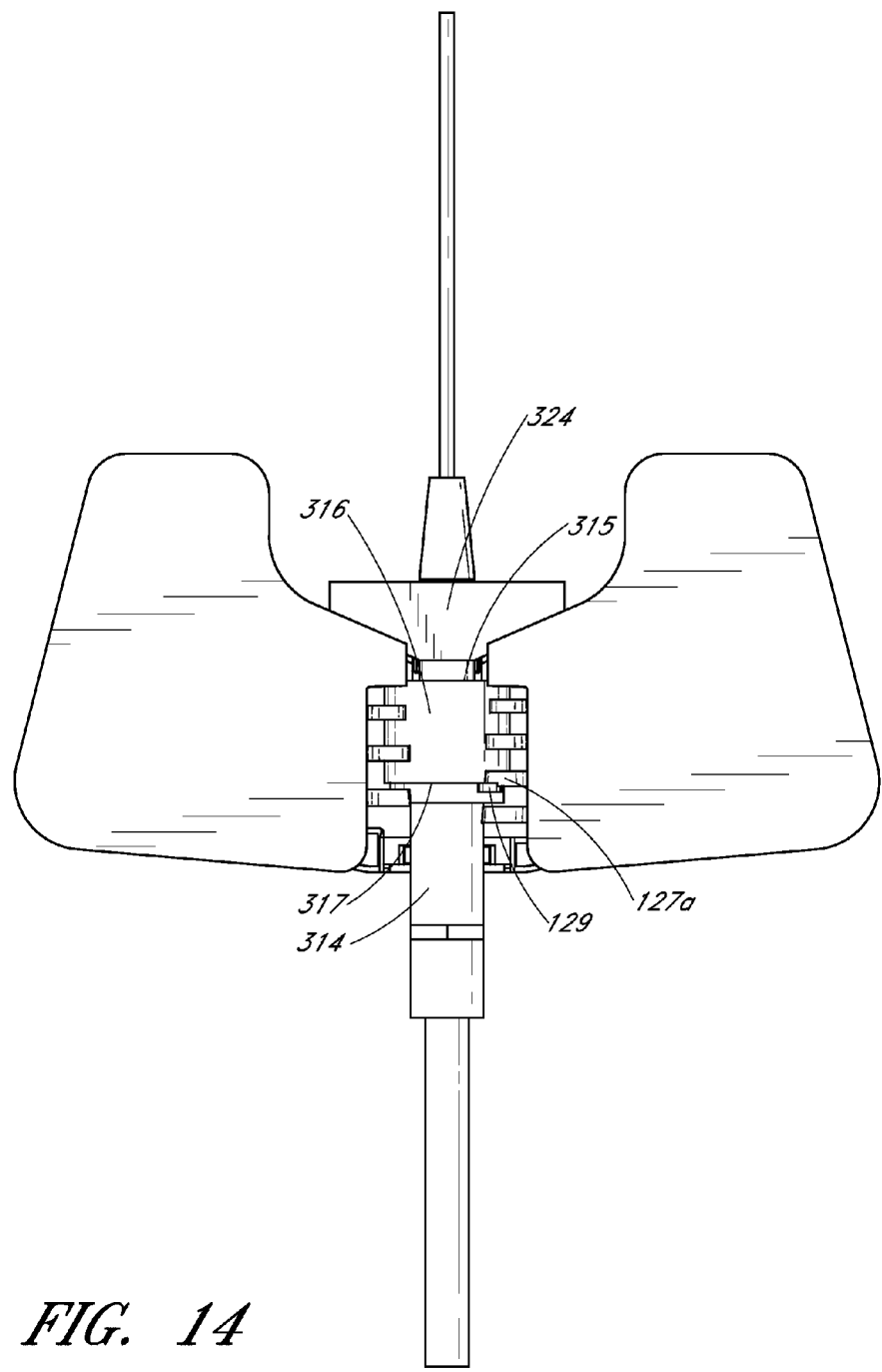
FIG. 14 is a bottom plan view of the securement device and medical article of FIG. 13.

As shown in FIGS. 13 and 14, the abutment feature 129 engages the distal facing surface 317 of the spin nut 316 so as to inhibit distal movement of the spin nut relative to the retainer 120 and/or the catheter hub 324. Thus, the abutment feature 129 may prevent inadvertent disengagement between the catheter hub 324 and the connector fitting 314. Additionally, the proximal facing surface 315 of the spin nut 316 contacts a distal facing surface of the proximal portion 123 of the retainer 120. Such engagement or contact can inhibit the proximal movement of the medical article 300 relative to the retainer 120 and/or an insertion site. Accordingly, the engagement between the proximal facing surface 315 and the retainer 120 can prevent an inadvertent vessel puncture caused by the proximal movement of the medical article 300 relative to an insertion site.

As shown in FIG. 13, in some embodiments, the catheter hub 324 can include one or more contact surfaces for abutting a proximal facing abutment surface of the proximal portion 123. For example, the proximal portion 123 can be aligned between the spin nut 316 and the catheter hub 324 such that the stabilization wings 326 contact the proximal facing abutment surface further limiting longitudinal movement of the medical article 300 relative to the retainer 120.

From the configuration shown in FIGS. 13 and 14, the securement device 100 can be attached to the patient using the anchor pads 210a, 210b with the medical article 300 secured therein. Once the spin nut 316 is connected to the catheter hub 324 and positioned within the retainer 120, the anchor pads 210a, 210b are secured to the patient. The spin nut 316 can be inserted into the retainer 120 either before or after the connector fitting 314 is attached to the hub 324.

Figure 15:
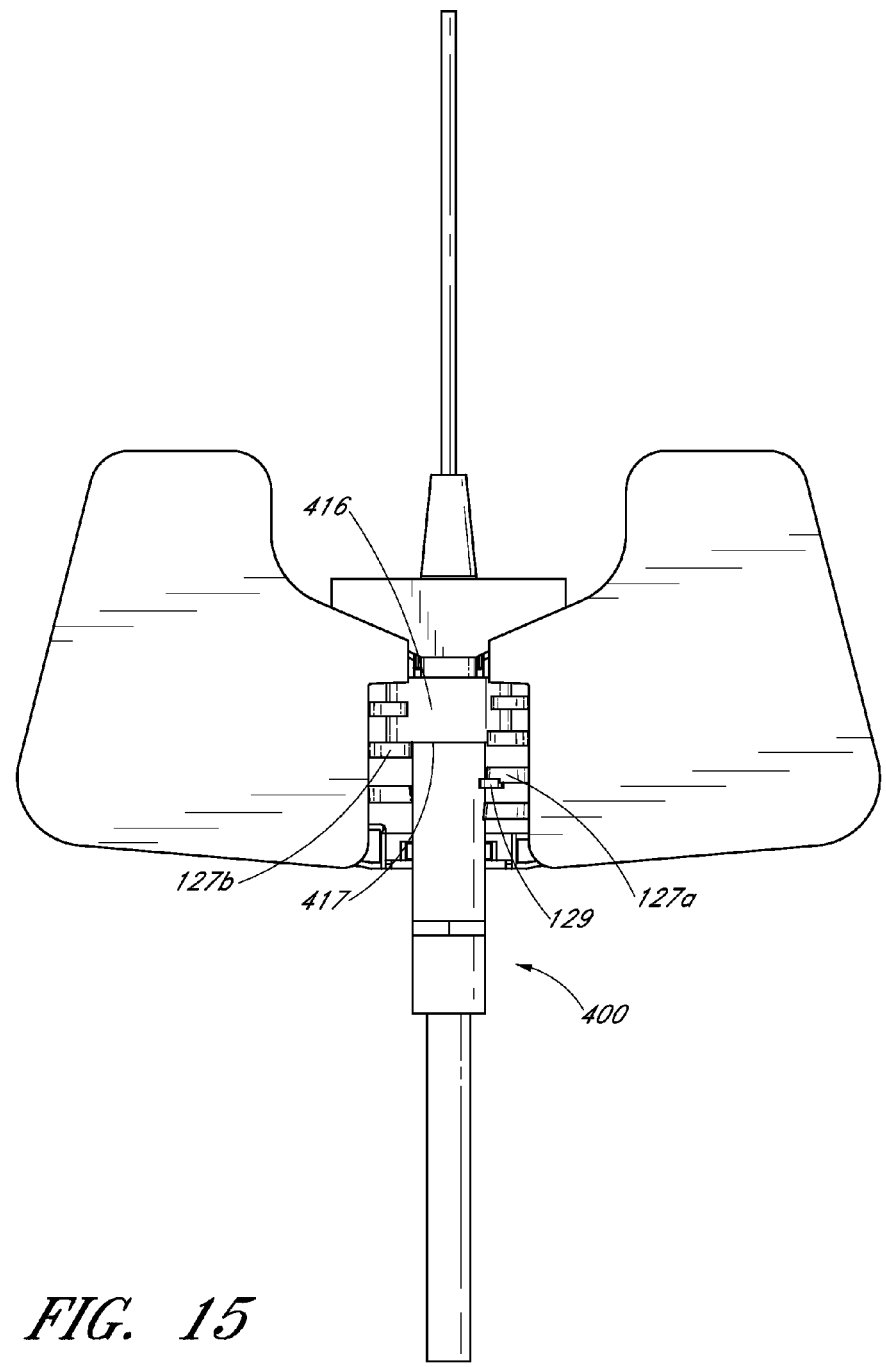
FIG. 15 is similar to FIG. 14 except that the medical article of FIG. 14 has been replaced with a medical article of a different size.

Turning now to FIG. 15, a bottom plan view of the securement device 100 is illustrated in conjunction with a different medical article 400. The medical article 400 includes components similar to the components of the medical article 300 illustrated in FIGS. 12 through 14. However, the longitudinal length of the spin nut 416 is less than the longitudinal length of spin nut 316. As a result, a distal facing surface 417 of the spin nut 416 is disposed nearer to the proximal portion 123 than the distal facing surface 317 of the spin nut 316.

As can be seen by comparing FIGS. 14 and 15, the same securement device 100 can accommodate differently sized and shaped medical articles. For example, due to the asymmetric staggering of the retention members 127, the distal facing surface 417 abuts a retention member 127b that is more proximal than the abutment feature 129. Thus, although the spin nut 416 is shorter than the spin nut 316, one of the retention members 127b may nevertheless abut the distal facing surface 417 so as to inhibit longitudinal movement of the medical article 400 in the distal direction. In this way, the securement device 100 can receive different configurations of medical articles and prevent or at least restrict longitudinal, transverse, and lateral movement of the medical articles relative to an insertion site.

Additional Embodiments

As understood from the above description of embodiment of the securement device shown in FIGS. 1 through 15, the securement device 100 arrests longitudinal movement of the retained section of the medical article by interacting with at least one contact surface of the medical article. In some embodiments this interaction can include the engagement of an abutment feature or abutment surface with a contact surface on a spin nut. For example, an engagement member can extend into the channel so as to abut a contact surface on the spin nut. To accommodate differently sized and shaped medical articles, the engagement members may be staggered laterally along the longitudinal axis of the channel such that the lateral sides of the retainer are asymmetric. Further, the medical article may be inserted into the channel by contacting the retention members so as to deflect the unsecured ends of the engagement members away from the channel axis and widen an opening through which the medical article may pass. The engagement members may return to the un-deflected state after the medical article has passed therebetween so as to support the medical article above the patient's skin. Further, the contact between retention surfaces of the retention members and the medical article may inhibit lateral and transverse movement of the medical article relative to the retainer.

Figure 17:
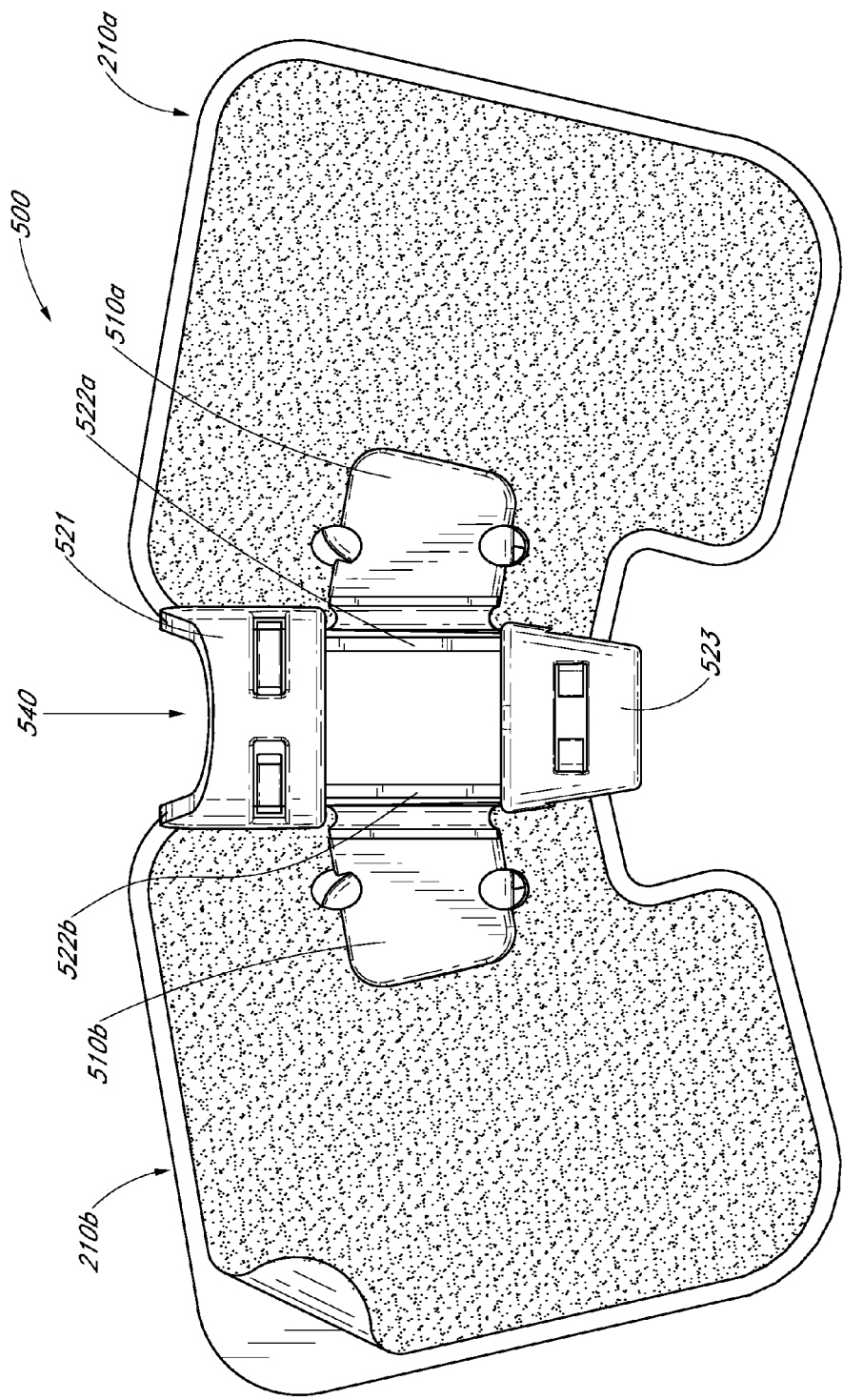
FIG. 17 is a top plan view of the securement device of FIG. 16.

FIGS. 16 through 30 illustrate another embodiment of a securement device 500. As shown in FIGS. 16 and 17, the securement device 500 comprises a retainer 520 having a proximal portion 523, a distal portion 521, and sidewalls 522a, 522b extending between the proximal portion and the distal portion. A channel 540 extends through the retainer 520 and is partially defined by the proximal portion 523, the distal portion 521, and the sidewalls 522a, 522b. The retainer 520 also includes a pair of supports 510a, 510b extending from the sidewalls 522a, 522b away from the channel 540. Each support 510 is disposed upon the respective one of anchor pads 210a, 210b which can be utilized to adhere the securement device 500 to a patient as discussed above.

Figure 18:
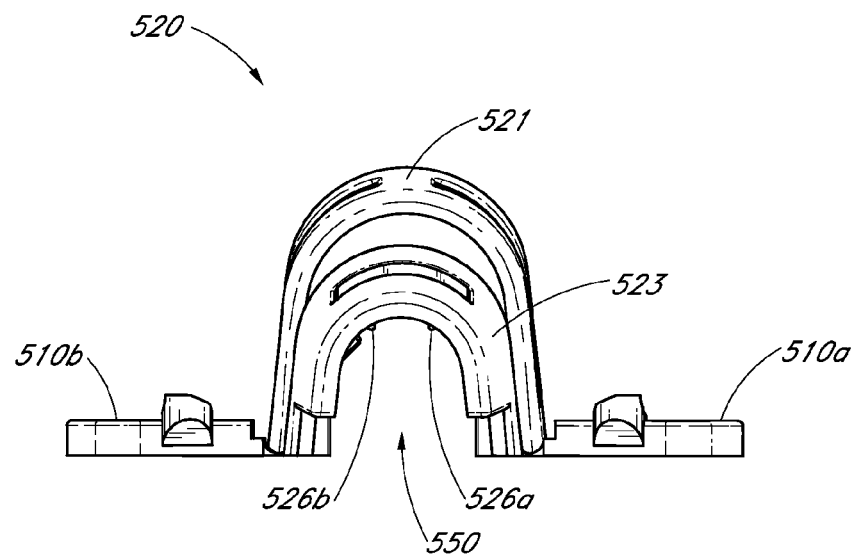
FIG. 18 is a front elevational view of the retainer from FIG. 17.
Figure 19:
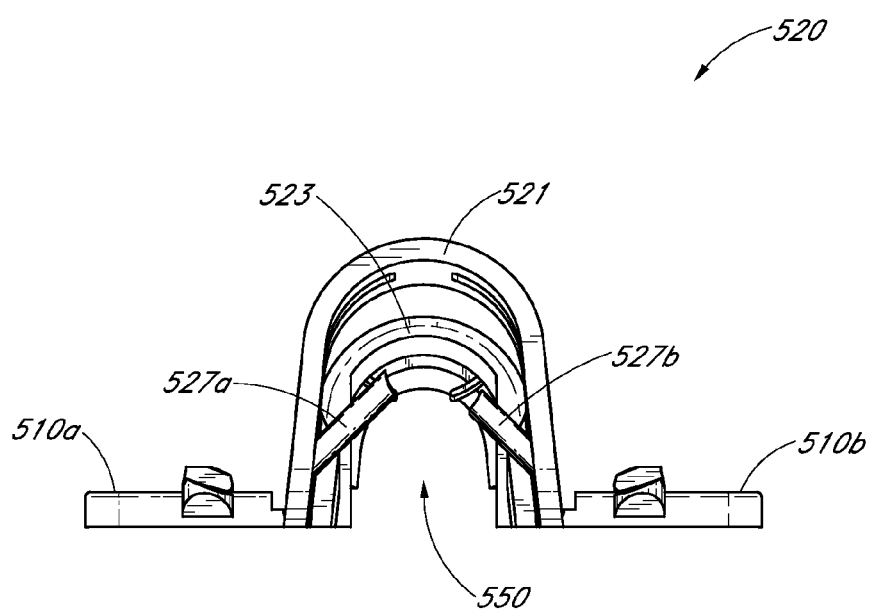
FIG. 19 is a rear elevational view of the retainer from FIG. 17.

As shown in FIGS. 18 and 19, the retainer includes a pair of retention members 527a, 527b extending into the channel 540 from sides of the distal portion 521. The retention members 527 may extend into the channel at an angle of 0-90° relative to the transverse axis of the retainer 520. Each of the retention members 527 includes a secured end coupled to the distal portion 521 and an opposite unsecured end disposed within the channel 540. In this way, the retention members 527 are cantilevered and the unsecured ends can be deflected relative to the channel axis. In some embodiments, the retention members 527a, 527b can have the same length measured between the unsecured ends and the secured ends. Alternatively, as illustrated, one of the retention members 527a may be longer than the other retention member 527b such that the retention members 527 extend into the channel 540 to different degrees.

Similar to the retention members 127 described above with reference to FIGS. 1-15, the retention members 527 are configured to engage a contact surface of a medical article so as to support the medical article above a patient's skin. The retention members 527 can include a retention surface for contacting the medical article. For example, a medical article may be inserted into the channel 540 through a longitudinal axis opening 550 disposed between the supports 510a, 510b. The medical article may contact the retention members 527 so as to deflect the unsecured ends of the retention members away from one another to allow the medical article to pass therebetween. After the medical article has passed through the unsecured ends of the retention members 527, the retention members 527 may return to an un-deflected configuration such that the retention surfaces engage a downward and/or lateral facing contact surface on the medical article. Depending on the angle of the un-deflected retention members 527 relative to the transverse axis of the retainer 520, the retention members may apply opposing lateral forces on the medical article so as to inhibit lateral movement of the medical article relative to the retainer. Further, in some embodiments, a retention member 527 can include an abutment feature or abutment surface for engaging a proximal or distal facing contact surface on the medical article. In this way, the retention members 527 can be configured to inhibit longitudinal, lateral, and transverse movement a retained portion of the medical article relative to the retainer 520.

Still referring to FIGS. 18 and 19, the retainer 520 includes fingers 526a, 526b extending into the channel 540 from the proximal portion 523. The fingers 526 can contact an upper facing surface of the retained portion of the medical article so as to inhibit further upward transverse movement of the retained portion away from the patient's skin. In some embodiments, the fingers 526 are configured as leaf springs so as to move between an extended configuration (see FIG. 19) when not in contact with the medical article and a compressed configuration when the medical article is positioned at least partially between the fingers and the retention members 527. In this way, the fingers 526 can act in concert to releasably grip and position the retained portion of the medical article within the channel 540.

Figure 20:
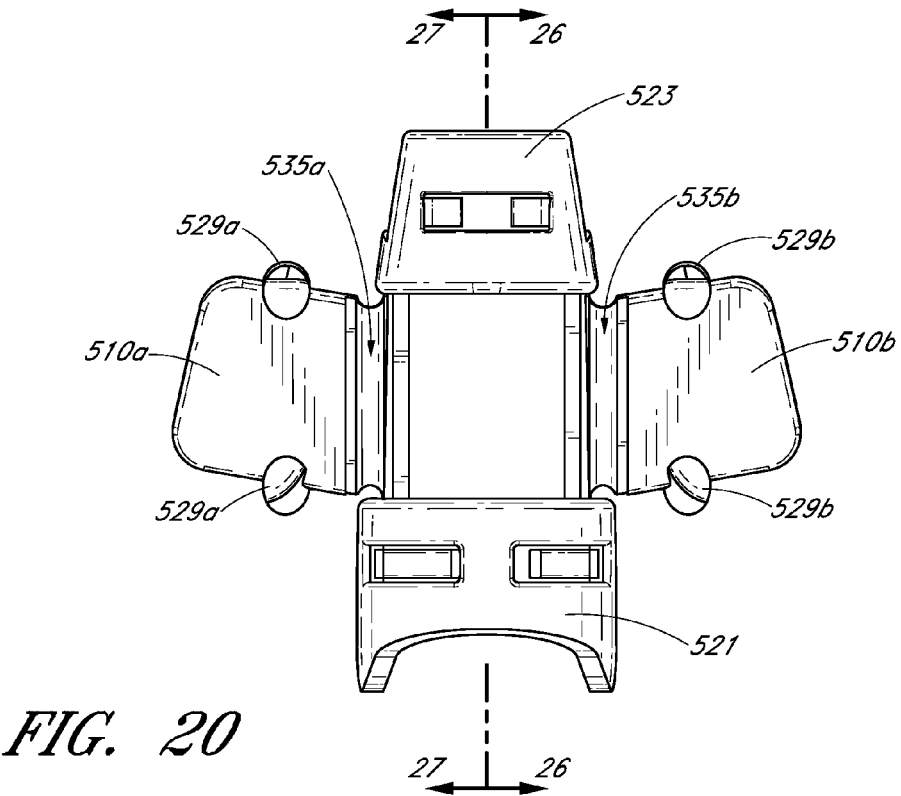
FIG. 20 is a top plan view of the retainer from FIG. 17.
Figure 21:
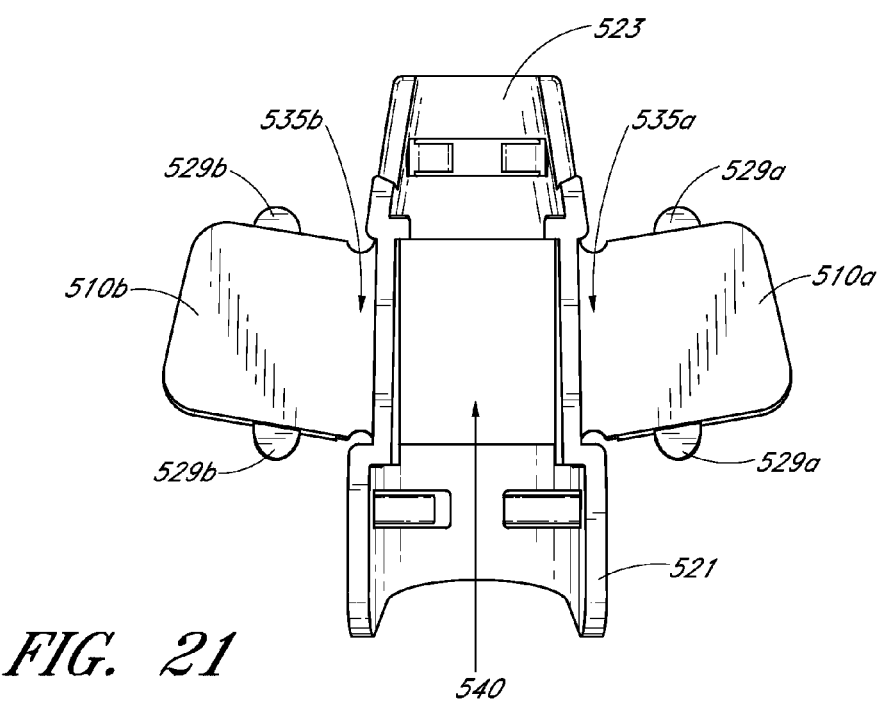
FIG. 21 is a bottom plan view of the retainer from FIG. 17.

As shown in FIGS. 20 and 21, each support 510a, 510b can be coupled to the respective sidewall 522a, 522b by a hinge portion 535. In this way, the supports 510 can be manipulated to rotate relative to the channel 540 about the hinge portions 535. In some embodiments, the hinge portions 535 comprise living hinges or thinned connections between the supports 510 and the sidewalls 522 such that the sidewalls and supports can be integrally formed. Each support 510 optionally includes one or more abutments 529 for engaging the proximal portion 523 and/or distal portion 521 of the retainer 520 when the upper surfaces of the supports are rotated toward the channel 540. For example, in the illustrated embodiment each support 510 includes an abutment 529 for contacting a surface of the proximal portion 523 and an abutment for contacting a surface of the distal portion 521.

Figure 22:
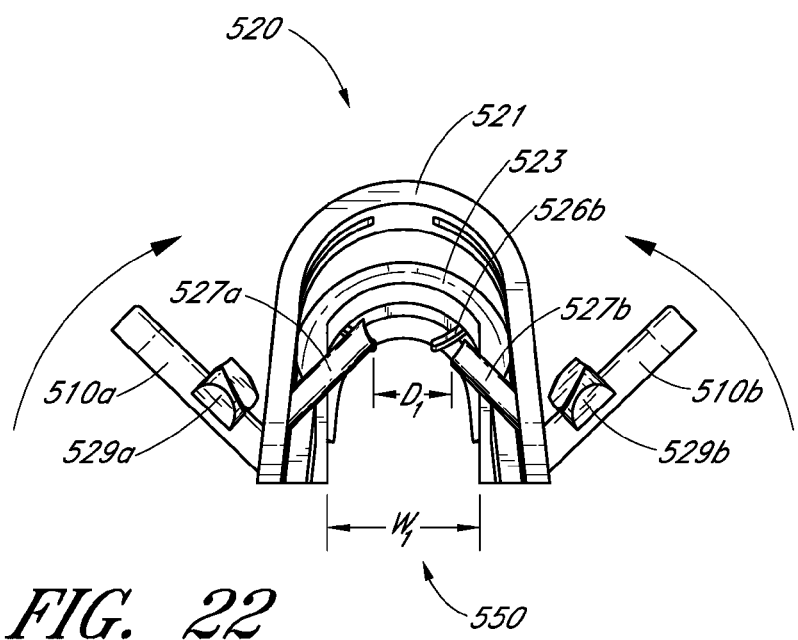
FIG. 22 is similar to FIG. 19 except that the supports are partially rotated in an upward direction to widen a lateral dimension of an opening into the retainer.
Figure 23:
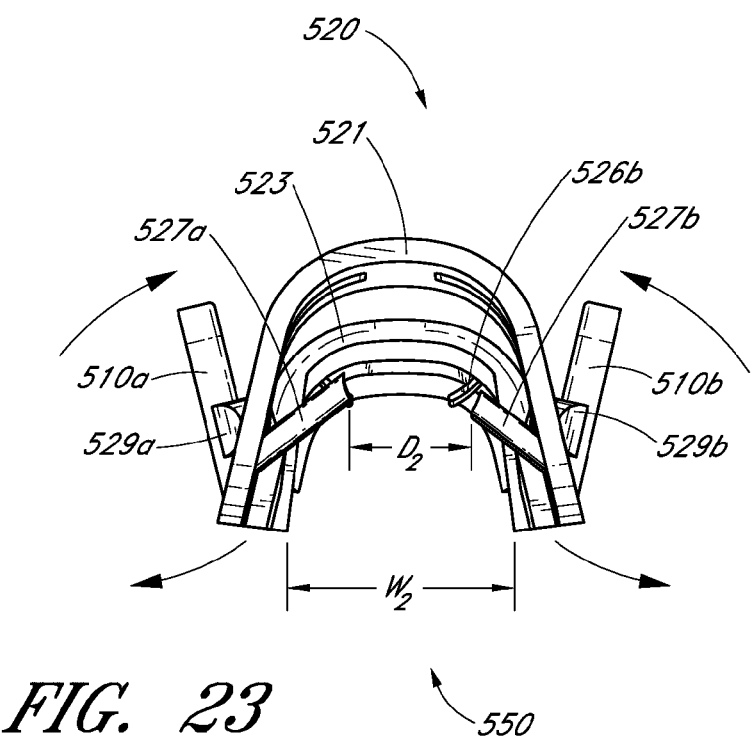
FIG. 23 is similar to FIG. 22 except that the supports have been further rotated so that the supports contact the retainer and widen the longitudinal access opening into the retainer.

FIGS. 22 and 23 illustrate how the supports 510 are manipulated to widen a lateral dimension of the longitudinal axis opening 550. As shown, the upper surfaces of the supports 510 may be rotated about the hinges 535 toward one another and toward the channel axis. When the abutments 529 contact the proximal portion 523 and distal portion 521, and the supports 510 are continually urged toward each other, the width of the channel between the lower lateral sides of the proximal portion 523 expands. That is to say, the supports 510 may act as lever arms to apply expanding forces to the proximal and distal portions at the abutments 529. This concept is shown be comparing FIGS. 22 and 23 where the width $W_1$ between the lower sides of the proximal portion 523 in FIG. 22 is less than the width $W_2$ in FIG. 23.

Another result of expanding the longitudinal access opening to the retainer 520 is the lateral separation of the retention members 527a, 527b is also increased. As shown in FIG. 22, a dimension $D_1$ between the unsecured ends of the retention members 527a, 527b is less than a dimension $D_2$ between the unsecured ends of the retention members in FIG. 23. Accordingly, manipulating the supports 510 about their hinges 535 can act to expand the access opening to the retainer in order to allow a medical article to pass between the retention members 527 when inserting the medical article into the retainer.

Figure 24:
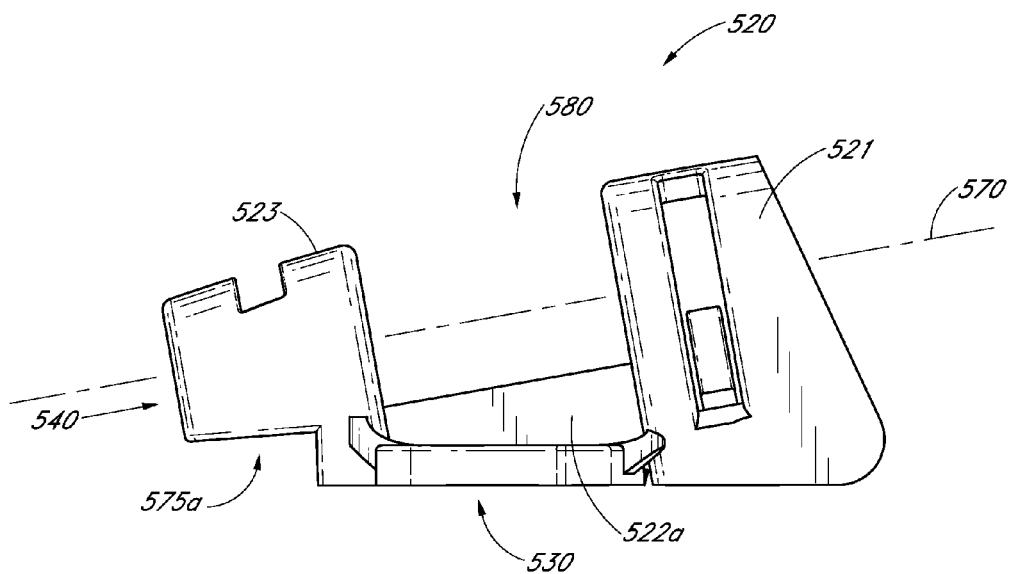
FIG. 24 is a right side elevational view of the retainer from FIG. 17.
Figure 25:
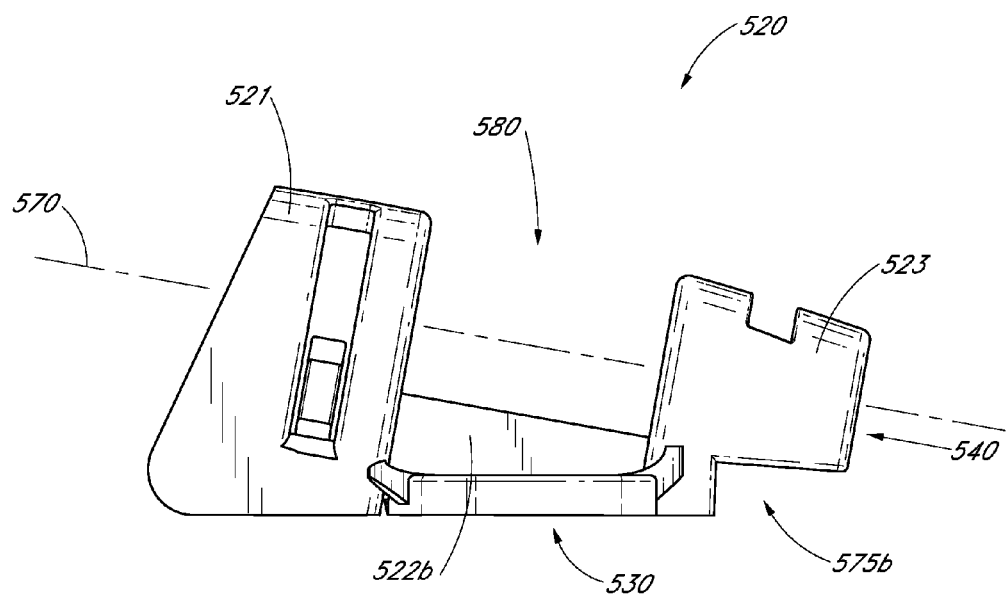
FIG. 25 is a left side elevational view of the retainer from FIG. 17.

FIGS. 24 and 25 are side views of the retainer 520. As illustrated, an axis 570 of the channel 540 lies at an angle with respect to the base surfaces 530 of the supports 510. The desired angle between the medical article and the patient is achieved by angling the axis 570 of the channel 540. This angle is preferably selected in order to align the axis 570 of the channel 540 with the desired incident angle with which the medical article is to contact the skin of the patient.

Figure 26:
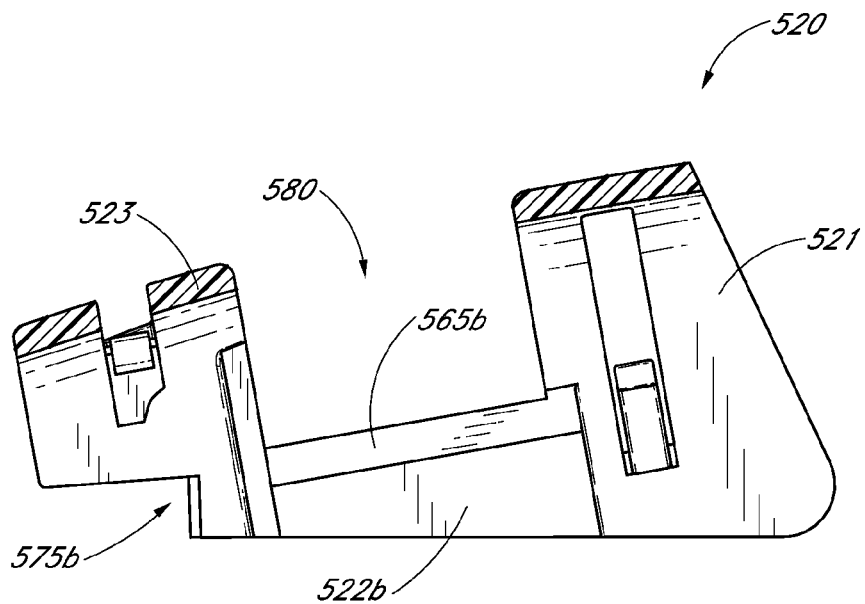
FIG. 26 is a cross-sectional view of the retainer taken along line 26-26 of FIG. 20.
Figure 27:
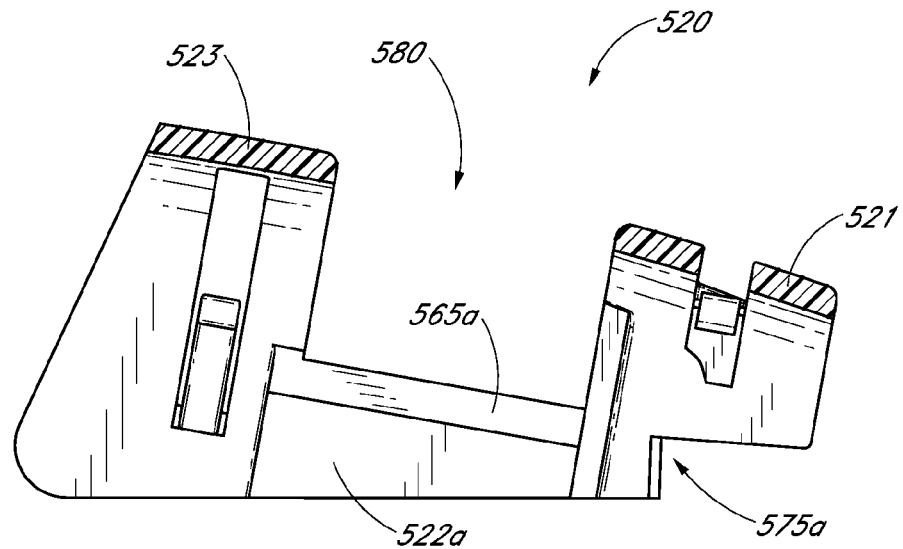
FIG. 27 is a cross-sectional view of the retainer taken along line 27-27 of FIG. 20.

FIGS. 26 and 27 are cross-sectional views illustrating retention surfaces 565 disposed on each of the sidewalls 522. The retention surfaces 565 can be configured to contact a portion of the medical article secured within the retainer 520. The retention surfaces 565 extend at an angle relative to the transverse axis of the retainer 520 so as to inhibit transverse and lateral movement of the medical article relative to the sidewalls. Further, as shown in FIGS. 24 and 25, the upper surfaces of the sidewalls 522 can extend parallel to axis 570. In this way, the retention surfaces 565 can support the medical article within the retainer 520 such that transverse and lateral movement of the medical article is inhibited while locating the medical article at a desired angle relative to the patient's skin.

As shown in FIGS. 24 through 27, the retainer 520 includes an access window or opening 580 disposed between the proximal portion 523 and the distal portion 521 above the sidewalls 522. This opening 580 allows the healthcare provider to access a retained portion of the medical article secured by the retainer 540 through the opening. Further, the opening 580 allows a healthcare provider to align a portion of the medical article to be received within the retainer 520 relative to the proximal portion 523 and the distal portion 521 by viewing the medical article through the opening. In some embodiments, a portion of the medical article may pass through the opening 580 away from the retainer 520 when secured by the securement device 500. For example, a transverse access port or tab can extend through the opening 580. In this way, the opening 580 may define at least a portion of a transverse channel that intersects the channel 540 extending through the distal portion 521 and the proximal portion 523.

In some embodiments, the proximal portion 521 can include one or more lateral slots 575 for receiving at least a portion of the medical article therethrough. As illustrated, the proximal portion 521 includes two opposing lateral slots 575a, 575b configured to receive a laterally extending portion of the medical article, for example, a stabilizing wing of a catheter hub. In this way, the slots 575 can abut or contact the medical article so as to further prevent or inhibit longitudinal, lateral, transverse, and/or rotational movement of the medical article relative to the retainer 520.

Figure 28:
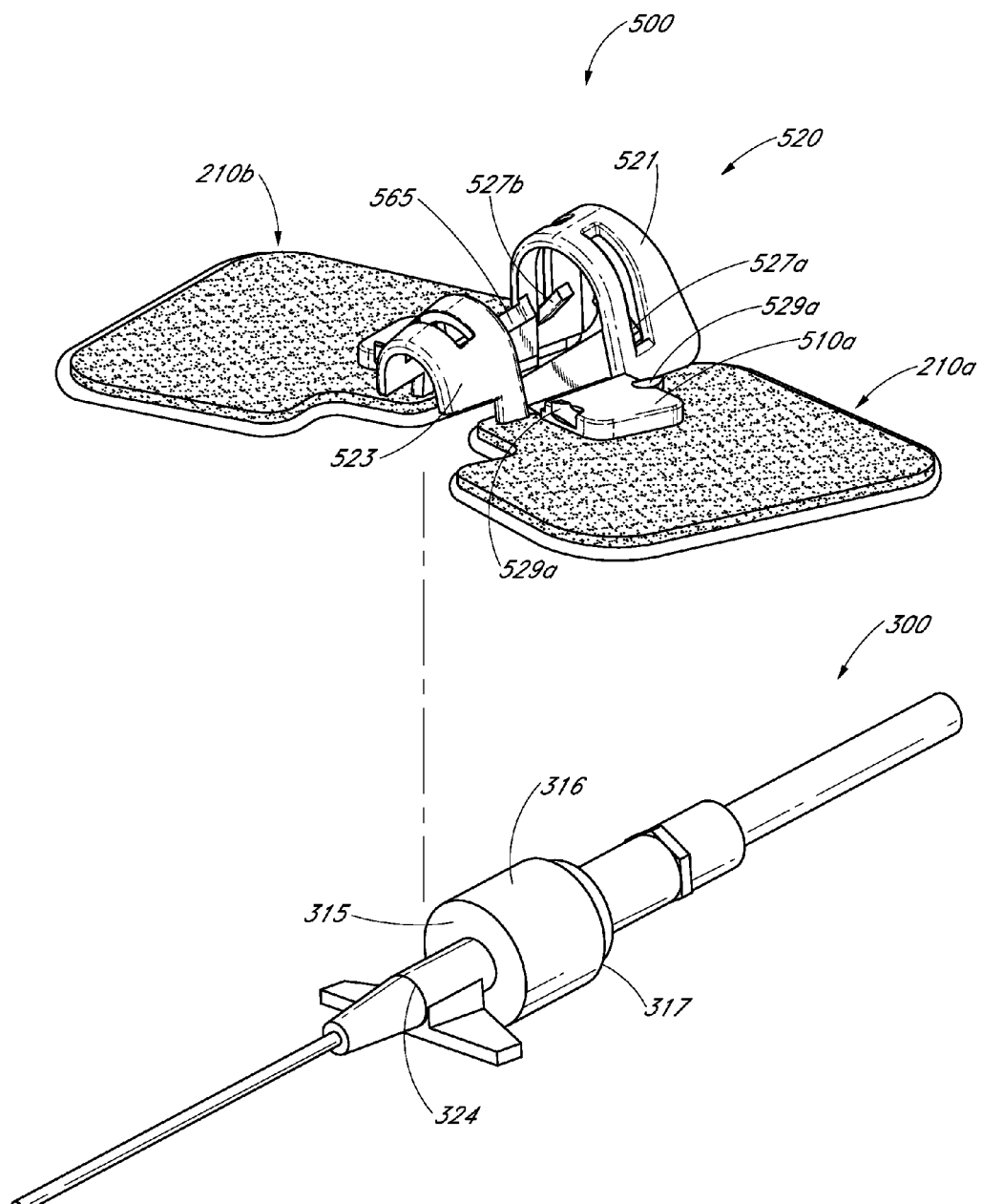
FIG. 28 is a perspective view of an exemplary medical article located below the securement device of FIG. 16 prior to insertion into the securement device.
Figure 29:
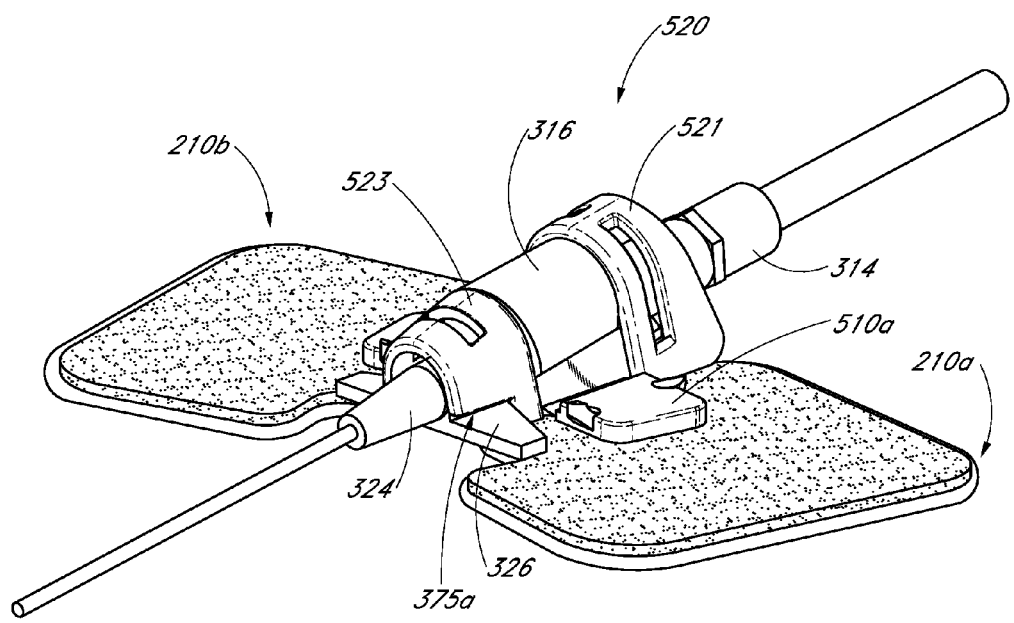
FIG. 29 is a perspective view of an exemplary medical article located below the securement device of FIG. 16 prior to insertion into the securement device.
Figure 30:
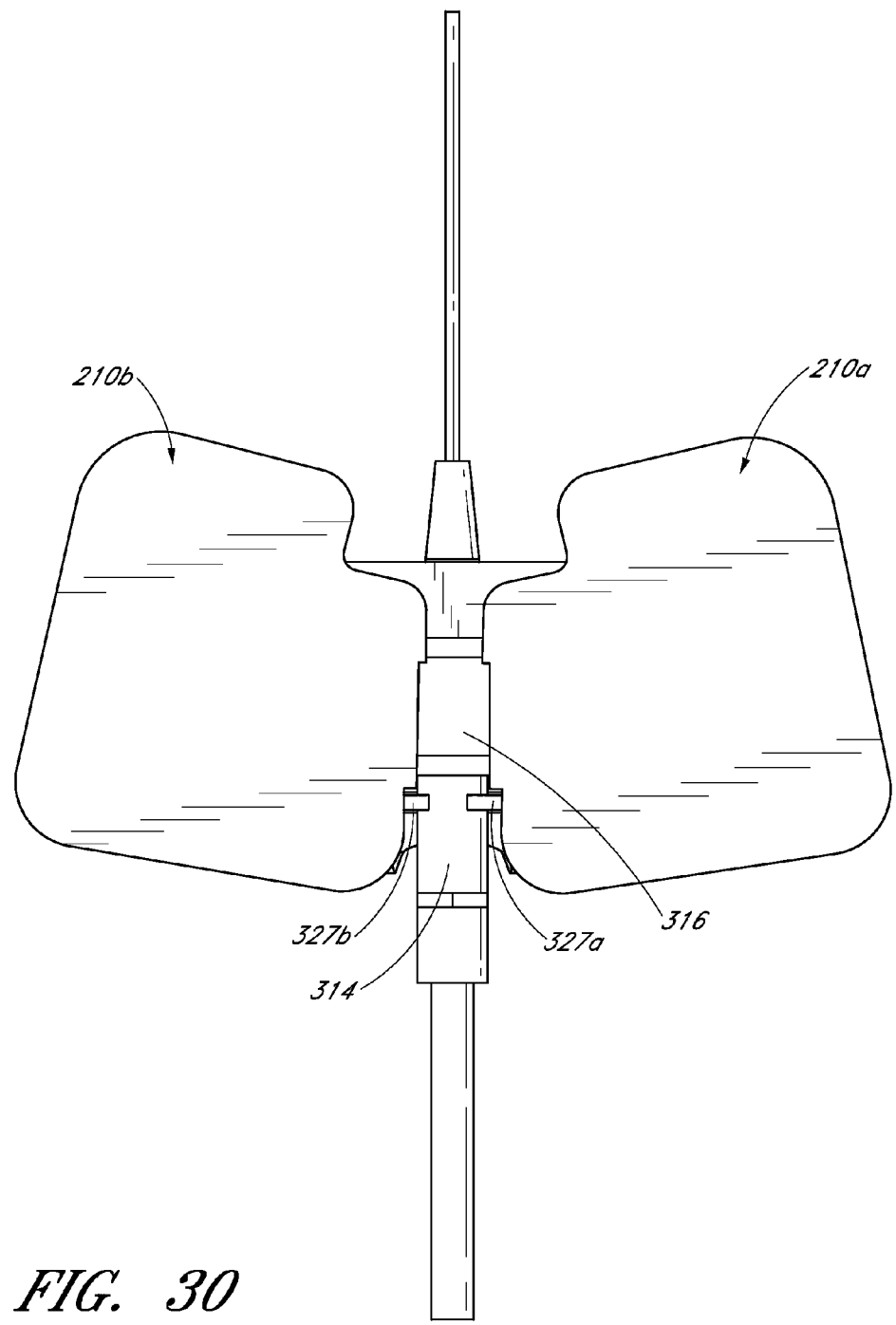
FIG. 30 is a bottom plan view of the securement device and medical article of FIG. 29.

FIGS. 28 through 30 illustrate the securement device 500 in use with the medical article 300 previously described above with reference to FIGS. 12 through 14. As shown, a portion of the medical article 300 including the spin nut 316 can be aligned between the proximal portion 523 and the distal portion 521 of the retainer 520 with the lumen of the medical article disposed between the anchor pads 210a, 210b. The opening between the anchor pads 210a, 210b may then be expanded by manipulating the upper surfaces of the supports 510a, 510b toward one another such that the abutments 529 contact the proximal portion 523 and distal portion 521. Such expansion acts to increase the distance between the unsecured ends of the retention members 527 to facilitate the insertion of the medical article 300 between the retention members.

As shown in FIGS. 29 and 30, after the medical article 300 has been placed within the retainer 520, the unsecured ends of the retention members 527 contact downward facing contact surfaces of the connector fitting 314 so as to inhibit lateral and transverse movement of the medical article 300 relative to the retainer 520. The fingers extending from the proximal portion 523 are compressed by the catheter hub 324 to releasably grip the medical article 300 between the fingers and the retention members 527. Additionally, the retention surfaces of the sidewalls 522 contact the spin nut 316 supporting the spin nut above the anchor pads 210a, 210b and inhibit lateral and transverse movement of the medical article 300.

As shown in FIG. 29, the proximal facing surface 315 of the spin nut 316 contacts a distal facing surface of the proximal portion 523 of the retainer 520. Such engagement or contact can inhibit the proximal movement of the medical article 300 relative to the retainer 520 and/or an insertion site. Furthermore, a proximal facing surface of the distal portion 521 of the retainer 520 can provide an abutment for the distal facing surface 317 of the spin nut 316. In this way, the longitudinal movement of the medical article 300 can be limited by one or more abutments between the proximal portion 523 and the spin nut 316 and/or between the distal portion 521 and the spin nut 316. Additionally, at least a portion of the stabilizing wings 326 extends through the slots 375 such that the wings contact the proximal portion 523. Thus, longitudinal, lateral, transverse, and rotational movement of the medical article relative to the retainer 520 is inhibited by the engagement between the slots 375 and the catheter hub 324.

From the position shown in FIGS. 29 and 30, the medical article 300 may be secured relative to the patient by adhering the anchor pads 210a, 210b to the patient's skin. The medical article 300 may then be released from the securement device 500 by removing the securement device from the patient's skin, manipulating the supports 510 to expand the longitudinal access opening to the retainer 520, and separating the medical article 300 from the retainer through the longitudinal access opening.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a securement device, and securement devices that include one or more of the features herein described can be designed for use with a variety of medical articles.

The various embodiments of the securement devices described above in accordance with the present invention thus provide a means to releasably secure a connector fitting or extension set to a patient. An insertion site of a catheter attached to the connector fitting or extension set may be covered with an integrated dressing.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct securement devices and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A retainer for securing a medical article, comprising:
    a body member having a channel formed therethrough along a longitudinal axis, the channel being configured to retain at least a portion of the medical article and having an access opening through a lateral underside of the body member to allow at least ingress of a portion of the medical article into the channel;
    first and second supports disposed on the underside of the retainer and located on opposite sides of the channel and of the access opening; and
    at least one retention member pivotably coupled to the body member or the first and second supports at a secured end, the at least one retention member having a distal end movable relative to the secured end so as to pivot in a transverse direction, at least a portion of the distal end being disposed in the channel so as to contact an outer surface of the portion of the medical article when the medical article is secured within the retainer.

2. The retainer of claim 1, wherein the distal end comprises a retention surface configured to engage a contact surface of the medical article.

3. The retainer of claim 2, wherein at least a portion of the retention surface is contoured so as to match a contact surface of the medical article.

4. The retainer of claim 2, wherein the retention surface includes at least an upper facing portion.

5. The retainer of claim 4, wherein the retention surface includes at least a lateral facing portion.

6. The retainer of claim 1, wherein the at least one retention member comprises an abutment surface extending generally normal to the axis of the channel, the abutment surface being disposed so as to inhibit longitudinal translation of the medical article relative to the retainer.

7. The retainer of claim 1, wherein the at least one retention member comprises a first retention member and a second retention member, the first retention member extending from the first support and the second retention member extending from the second support.

8. The retainer of claim 7, wherein the first retention member and the second retention member are staggered laterally along the axis of the channel.

9. The retainer of claim 7, wherein a length of the first retention member is different than a length of the second retention member.

10. The retainer of claim 7, wherein a distal end of the first retention member is movable relative to a distal end of the second retention member.

11. The retainer of claim 1, wherein the at least one retention member is movable between at least a first position and a second position, the at least one retention member being biased toward the first position.

12. The retainer of claim 1, wherein the at least one retention member is coupled to one of the first and second supports via a living hinge.

13. An apparatus for retaining a portion of a medical article, the apparatus comprising:
    a body having a channel extending therethrough about a longitudinal axis, the channel being shaped to retain at least a portion of the medical article and having an access opening through a lateral underside of the body;
    a first support and a second support located on the underside of the body and on opposite sides of the channel and of the access opening;
    a plurality of retention members extending from the first and second supports and into the channel, the plurality of retention members being spaced along the longitudinal axis, each of the retention members having a secured end and an unsecured end, the unsecured end being movable relative to the secured end so as to pivot in a transverse direction; and
    a pair of anchors comprising lower adhesive surfaces configured to be secured to the skin of a patient, the anchors supporting the retainer.

14. The apparatus of claim 13, wherein the body comprises a proximal portion extending between the first and second supports and over the channel and a distal portion extending between the first and second supports and over the channel.

15. The apparatus of claim 14 further comprising a finger extending downward from the proximal portion into the channel, the finger being compressible in an upward direction.

16. The apparatus of claim 14, wherein the proximal portion and the distal portion at least partially define an opening therebetween, the opening being sized to receive at least a portion of an outwardly extending member of the medical article.

17. The apparatus of claim 14, wherein at least one of the proximal portion and the distal portion comprises at least one abutment surface configured to contact an outwardly extending member of the medical article so as to inhibit longitudinal movement of the medical article relative to the retainer.

18. The apparatus of claim 13, wherein the plurality of retention members comprises a first set of retention members extending from the first support.

19. The apparatus of claim 18, wherein the plurality of retention members comprises a second set of retention members extending from the second support.

20. The apparatus of claim 19, wherein the first set of retention members and the second set of retention members are staggered laterally along the longitudinal axis such that the retainer is asymmetric across the longitudinal axis.

21. A method for releasably anchoring an elongated medical article, the method comprising:
    providing a retainer having a body comprising at least one retention member, a channel which extends through at least a portion of the body and along a longitudinal axis, an access opening through a lateral underside of the body to allow at least ingress of a portion of the medical article into the channel, the at least one retention member being pivotably coupled to the body at a secured end, the at least one retention member extending into the channel and having a distal end, the distal end being movable relative to the secured end so as to pivot in a transverse direction between at least a first position and a second position, and first and second supports disposed on the underside of the retainer and located on opposite sides of the channel and of the access opening;
    inserting the portion of the medical article between the first and second supports and through the access opening and into the channel; and
    deflecting the at least one retention member from the first position to the second position so as to secure the medical article in the channel.

* * * * *